(12) United States Patent
Kawai et al.

(10) Patent No.: US 9,506,894 B2
(45) Date of Patent: Nov. 29, 2016

(54) METHOD FOR CONTROLLING SUBSTANCE MOVING SPEED AND APPARATUS FOR CONTROLLING THE SAME

(71) Applicant: Quantum Biosystems Inc., Tokyo (JP)

(72) Inventors: Tomoji Kawai, Osaka (JP); Soh Ryuzaki, Osaka (JP); Masateru Taniguchi, Osaka (JP)

(73) Assignee: QUANTUM BIOSYSTEMS INC., Tokyo (JP)

( * ) Notice: Subject to any disclaimer, the term of this patent is extended or adjusted under 35 U.S.C. 154(b) by 473 days.

(21) Appl. No.: 13/975,610

(22) Filed: Aug. 26, 2013

(65) Prior Publication Data

US 2014/0183040 A1    Jul. 3, 2014

(30) Foreign Application Priority Data

Dec. 27, 2012 (JP) ................. 2012-286115

(51) Int. Cl.
   *G01N 27/447*    (2006.01)
   *G01N 33/487*    (2006.01)

(52) U.S. Cl.
   CPC .. *G01N 27/44756* (2013.01); *G01N 27/44752* (2013.01); *G01N 33/48721* (2013.01)

(58) Field of Classification Search
   CPC ............... G01N 33/48721; G01N 27/44791; G01N 27/44752
   See application file for complete search history.

(56) References Cited

U.S. PATENT DOCUMENTS

| | | |
|---|---|---|
| 5,092,972 A | 3/1992 | Ghowsi |
| 5,122,248 A | 6/1992 | Karger et al. |
| 5,151,164 A | 9/1992 | Blanchard et al. |
| 5,262,031 A | 11/1993 | Lux et al. |
| 5,593,838 A | 1/1997 | Zanzucchi et al. |
| 5,906,723 A | 5/1999 | Mathies et al. |
| 6,159,353 A | 12/2000 | West et al. |
| 6,491,805 B1 | 12/2002 | Gordon et al. |
| 6,613,513 B1 | 9/2003 | Parce et al. |
| 7,033,476 B2 | 4/2006 | Lee et al. |
| 7,892,414 B1 | 2/2011 | Sumner |
| 7,918,979 B2 | 4/2011 | Han et al. |

(Continued)

FOREIGN PATENT DOCUMENTS

| | | |
|---|---|---|
| JP | H 0774337 A | 3/1995 |
| JP | 2003/090815 A | 3/2003 |

(Continued)

OTHER PUBLICATIONS

He et al. "Controlling DNA Translocation through Gate Modulation of Nanopore Wall Surface Charges", ACSNano, vol. 5, No. 7, pp. 5509-5518, 2011.*

(Continued)

*Primary Examiner* — Alexander Noguerola
(74) *Attorney, Agent, or Firm* — Wilson Sonsini Goodrich & Rosati

(57) ABSTRACT

The present invention provides a method and apparatus for controlling the moving speed of a substance, both of which can adjust the moving speed of a substance to a desired speed. The control method and control apparatus cause a substance to pass through an internal space, in which an electro-osmotic flow is generated, of a surround electrode formed so as to surround part of the moving path of the substance, whereby the control method and control apparatus change the moving speed of the substance.

29 Claims, 13 Drawing Sheets

(56) References Cited

U.S. PATENT DOCUMENTS

| | | |
|---|---|---|
| 8,333,934 B2 | 12/2012 | Cao et al. |
| 9,194,838 B2 | 11/2015 | Taniguchi et al. |
| 2001/0046681 A1 | 11/2001 | Senapathy |
| 2003/0085719 A1 | 5/2003 | Yoon et al. |
| 2003/0089606 A1 | 5/2003 | Parce et al. |
| 2003/0141189 A1 | 7/2003 | Lee et al. |
| 2004/0144658 A1 | 7/2004 | Flory |
| 2005/0048513 A1 | 3/2005 | Harwit et al. |
| 2005/0061669 A1 | 3/2005 | Woudenberg et al. |
| 2005/0127035 A1 | 6/2005 | Ling |
| 2005/0136419 A1 | 6/2005 | Lee |
| 2005/0202444 A1 | 9/2005 | Zhu |
| 2005/0202446 A1 | 9/2005 | Yang et al. |
| 2006/0057585 A1 | 3/2006 | McAllister |
| 2006/0210995 A1 | 9/2006 | Joyce |
| 2007/0029911 A1 | 2/2007 | Hudspeth et al. |
| 2007/0042366 A1 | 2/2007 | Ling |
| 2009/0155917 A1 | 6/2009 | Umezawa et al. |
| 2009/0215156 A1 | 8/2009 | Chung et al. |
| 2009/0242429 A1 | 10/2009 | Sitdikov et al. |
| 2010/0025249 A1 | 2/2010 | Polonsky et al. |
| 2010/0066348 A1 | 3/2010 | Merz et al. |
| 2010/0084276 A1 | 4/2010 | Lindsay |
| 2010/0184062 A1 | 7/2010 | Steinmuller-Nethl et al. |
| 2010/0188109 A1 | 7/2010 | Edel et al. |
| 2010/0243449 A1 | 9/2010 | Oliver |
| 2010/0292101 A1 | 11/2010 | So |
| 2010/0331194 A1 | 12/2010 | Turner et al. |
| 2011/0056845 A1 | 3/2011 | Stellacci et al. |
| 2011/0236984 A1 | 9/2011 | Sun et al. |
| 2011/0250464 A1 | 10/2011 | Wilson et al. |
| 2011/0287956 A1 | 11/2011 | Iqbal et al. |
| 2012/0041727 A1 | 2/2012 | Mishra et al. |
| 2012/0097539 A1* | 4/2012 | Qian ............... G01N 33/48721 204/451 |
| 2012/0132886 A1 | 5/2012 | Peng et al. |
| 2012/0193237 A1 | 8/2012 | Afzali-Ardakani et al. |
| 2012/0199485 A1 | 8/2012 | Sauer et al. |
| 2012/0254715 A1 | 10/2012 | Schwartz |
| 2012/0322055 A1 | 12/2012 | Royyuru |
| 2013/0001082 A1 | 1/2013 | Afzali-Ardakani et al. |
| 2013/0092547 A1 | 4/2013 | Li et al. |
| 2014/0001055 A1 | 1/2014 | Elibol et al. |
| 2014/0031995 A1 | 1/2014 | Kawai et al. |
| 2014/0055150 A1 | 2/2014 | Kawai et al. |
| 2014/0300339 A1 | 10/2014 | Taniguchi et al. |
| 2014/0374695 A1 | 12/2014 | Astier et al. |
| 2015/0219593 A1 | 8/2015 | Kawai et al. |
| 2016/0049327 A1 | 2/2016 | Singh et al. |
| 2016/0138101 A1 | 5/2016 | Taniguchi et al. |
| 2016/0245789 A1 | 8/2016 | Ikeda et al. |
| 2016/0245790 A1 | 8/2016 | Kawai et al. |

FOREIGN PATENT DOCUMENTS

| | | |
|---|---|---|
| JP | 2003/332555 A | 11/2003 |
| JP | 2003/533676 A | 11/2003 |
| JP | 2004/233356 A | 8/2004 |
| JP | 2005/257687 A | 9/2005 |
| JP | 2006/078491 A | 3/2006 |
| JP | 2006/526777 A | 11/2006 |
| JP | 2007/272212 A | 10/2007 |
| JP | 2008/032529 A | 2/2008 |
| JP | 2008/186975 A | 8/2008 |
| JP | 2008/536124 A | 9/2008 |
| JP | 2009/527817 A | 7/2009 |
| JP | 2010/513853 A | 4/2010 |
| JP | 2011/500025 A | 1/2011 |
| JP | 2011/054631 A | 3/2011 |
| JP | 2011/516050 A | 5/2011 |
| JP | 2011/163934 A | 8/2011 |
| JP | 2013/036865 A | 2/2013 |
| WO | WO 01/81908 A1 | 11/2001 |
| WO | WO 03/018484 A1 | 3/2003 |
| WO | WO 2007/013370 A1 | 2/2007 |
| WO | WO 2009/093019 A2 | 7/2009 |
| WO | WO 2009/120642 A1 | 10/2009 |
| WO | WO 2010/116595 A1 | 10/2010 |
| WO | WO 2011/082419 A1 | 7/2011 |
| WO | WO 2011/108540 A1 | 9/2011 |
| WO | WO 2013/100949 A1 | 7/2013 |
| WO | WO 2013/116509 A1 | 8/2013 |

OTHER PUBLICATIONS

Nam et al., "Ionic Field Effect Transistors with Sub-10 nm Multiple Nanopores", Nano Letters 2009, vol. 9, No. 5, pp. 2044-2048.*
U.S. Appl. No. 14/421,809, filed Feb. 13, 2015, Kawai.
International search report and written opinion dated Oct. 29, 2013 for PCT Application No. JP2013/071059.
Furuhashi, et al. High speed DNA denaturation using microheating devices. Appl. Phys. Lett., Jul. 11, 2013, 103, pp. 023112.
International search report dated Feb. 24, 2015 for PCT Application No. IB2014/002128.
Kaji, et al. Separation of long DNA molecules by quartz nanopillar chips under a direct current electric field. Anal. Chem., Jan. 1, 2004, 76(1): pp. 15-22.
Nadasan, et al. Design and fabrication of the microchannels for microfluidics applications. U.P.B. Sci. Bull., Series C, 2009, 71(4): pp. 125-34.
U.S. Appl. No. 14/687,856, filed Apr. 15, 2015, Ikeda.
International Preliminary Report on Patentability dated Jun. 25, 2013 for PCT Application No. JP2013/059645.
International search report and written opinion dated Jan. 26, 2015 for PCT Application No. US2014/060742.
International search report dated Feb. 17, 2015 for PCT Application No. IB2014/002143.
International search report dated Jun. 25, 2013 for PCT Application No. JP2013/059645.
Office action dated Apr. 17, 2015 for U.S. Appl. No. 13/992,328.
Taniguchi, et al. Denryu de Ichi Enki Bunshi o Shikibetsu suru. Chemistry, 2011, vol. 66, No. 8, pp. 42-46.
Taniguchi, M. Ichibunshi Kaiseki Gijutsu ni yoru Jijisedai DNA Sequencer no Kaihatsu. Dai 69 Kai Hyomen Kagaku Kenkyukai Yoshishu. Mar. 9, 2011, pp. 23-26.
Zhou, et al. Microfabrication of a mechanically controllable break junction in silicon. Appl. Phys. Lett. 67, 1160 (1995).
Notice of allowance dated Oct. 8, 2015 for U.S. Appl. No. 13/992,328.
U.S. Appl. No. 14/883,494, filed Oct. 14, 2015, Taniguchi et al.
Troisi, et al. Molecular signatures in the transport properties of molecular wire junctions: what makes a junction "molecular"? Small. Feb. 2006;2(2):172-81.
Bagci, et al. Recognizing nucelotides by cross-tunneling currents for DNA sequencing. Physical Review E, vol. 84, Issue No. 1, Article No. 011917 (internal pp. 1-4) (2011).
International search report and written opinion dated Dec. 19, 2014 for PCT Application No. US2014/056173.
Oshiro, et al. Detection of post-translational modifications in single peptides using electron tunnelling currents. Nature Nanotechnology, vol. 9, pp. 835-840 (e-pub. Sep. 14, 2014).
Oshiro, et al. Single-molecule electrical random resequencing of DNA and RNA. Scientific Reports, vol. 2, Article No. 501 (internal pp. 1-7) (e-pub. Jul. 10, 2012) See abstract: p. 2; figures 1-4; and tables 1-3.
Branton, et al. The potential and challenges of nanopore sequencing. Nature Biotechnology, vol. 26, No. 10, Oct. 2008, pp. 1146-1153.
Brown, et al. Nucleotide—Surface Interactions in DNA-Modified Au—Nanoparticle Conjugates: Sequence Effects on Reactivity and Hybridization. J. Phys. Chem. C, 2008, 112 (20), pp. 7517-7521.
Chang, et al. Tunnelling readout of hydrogen-bonding-based recognition. Nature Nantechnology, vol. 4, May 2009, pp. 297-301.
Dekker, et al. Solid-state nanopores. Nature Nanotechnology, vol. 2, Apr. 2007, pp. 209-215.
Fischbein, et al. Sub-10 nm Device Fabrication in a Transmission Electron Microscope. American Chemical Society, Nano Letters, 2007, vol. 7, No. 5, pp. 1329-1337.

(56) References Cited

OTHER PUBLICATIONS

Fologea, et al. Detecting Single Stranded DNA with a Solid State Nanopore. American Chemical Society, Nano Letters, 2005, vol. 5, No. 10, pp. 1905-1909.

He, et al. Identification of DNA Basepairing via Tunnel-Current Decay. American Chemical Society, Nano Letters, 2007, vol. 7, No. 12, pp. 3854-3858.

Keyser, et al. Direct force measurements on DNA in a solid-state nanopore. Nature Physics, vol. 2, Jul. 2006, pp. 473-477.

Lagerqvist, et al. "Fast DNA Sequencing via Transverse Electronic Transport", American Chemical Society, Nano Letters, 2006, vol. 6, No. 4, pp. 779-782.

Lagerqvist, et al. Influence of the Environment and Probes on Rapid DNA Sequencing via Transverse Electronic Transport. Biophysical Journel, vol. 93, Oct. 2007, pp. 23842390.

Li, et al. Ion-beam sculpting at nanometer length scales. Nature, vol. 412, Jul. 2001, pp. 166-169.

Liang, et al. Nanogap Detector Inside nanofluidic Channel for Fast Real-Time Label-Free DNA Analysis. American Chemical Society, Nano Letters 2008, vol. 8, No. 5, pp. 1472-1476.

Maleki, et al. A nanofluidic channel with embedded transverse nanoelectrodes. Nanotechnology, 20, (2009) 105302, pp. 1-6.

Pedone, et al. Data Analysis of Translocation Events in Nanopore Experiments. American Chemical Society, Anal. Chem. 2009, 81, pp. 9689-9694.

Peng, et al. Reverse DNA translocation through a solid-state nanopore by magnetic tweezers. Nanotechnology. May 6, 2009;20(18):185101. doi: 10.1088/0957-4484/20/18/185101. Epub Apr. 14, 2009.

Ruitenbeek, et al. Adjustable nanofabricated atomic size contacts. Rev. Sci. Instrum. 67, 108 (1996).

Simmons, et al. Generalized Formula for the Electric tunnele Effect between Similar Electrodes Separated by a Thin Insulating Film. J. Appl. Phys. 34, 1793 (1963).

Stijin Van Dorp, et al. Origin of the electrophoretic force on DNA in solid-state nanopores. Nature Physics, vol. 5, May 2009, pp. 347-351.

Stoddart, et al. Single-nucleotide discrimination in immobilized DNA oligonucleotides with a biological nanopore. PNAS, May 12, 2009, vol. 106, No. 19, pp. 7702-7707.

Storm, et al. Fabrication of solid-state nanopores with single-nanometere precision. Nature Materials, Vol2, Aug. 2003, pp. 537-540.

Taniguchi, et al. Development of Single-Molecule Bio-Nanodevies for Medical Applications. The Imaging Society of Japan, Feb. 10, 2013, vol. 52, No. 1, pp. 51-60.

Trepagnier, et al. Controlling DNA Capture and Progagation through Artificial Nanopores. American Chemical Society, Nano Letters, 2007, vol. 7, No. 9, pp. 2824-2830.

Tsutsui, et al. Fabrication of 0.5 nm electrode gaps using self-breaking technique. Applied Physics Letters 93, 163115 (2008); DOI: 10.1063/1.3006063.

Tsutsui, et al. Formation and self-breaking mechanism of stable atom-sized junctions. Nano Lett. Jan. 2008;8(1):345-9. Epub Dec. 21, 2007.

Tsutsui, et al. Identifying single nucleotides by tunnelling current. Nature Nanotechnology, Letters, Published Online. Mar. 21, 2010; DOI: 10.1038/NNAN0.2010.42, pp. 1-5.

Tsutsui, et al. Transverse Field Effects on DNA-Sized Particle Dynamics. American Chemical Society, Nano Letters, 2009, vol. 9, No. 4, pp. 1659-1662.

Wang, et al. Mechanism of electron conduction in self-assembled alkanethiol monolayer devices. Phys. Rev. B 68, 035416—Published Jul. 17, 2003.

Yen, et al. Gate effects on DNA translocation through silicon dioxide nanopore. Rev Sci Instrum. Mar. 2012;83(3):034301. doi: 10.1063/1.3692746.

Zwolak, et al. Colloquium: Physical approaches to DNA sequencing and detection Reviews of Modern Physics, vol. 80, Jan.-Mar. 2008, pp. 141-165.

Zwolak, et al. Electronic Signature of DNA Nucleotides via Transverse Transport. American Chemical Society, Nano Letters, 2005, vol. 5, No. 3, pp. 421-424.

Clarke et al., "Continuous base identification for single-molecule nanopore DNA sequencing", Nature Nanotechnology, vol. 4, Apr. 2009, pp. 265-270, Published online: Feb. 22, 2009/DOI: 10.1038/NNANO.2009.12.

Huang, et al. Identifying single bases in a DNA oligomer with electron tunnelling. Nat Nanotechnol. Dec. 2010;5(12):868-73. doi: 10.1038/nnano.2010.213. Epub Nov. 14, 2010.

Notice of allowance dated Jul. 17, 2015 for U.S. Appl. No. 13/992,328.

Office action dated Sep. 1, 2015 for U.S. Appl. No. 14/112,189.

Carter, et al. Voltammetric studies of the interaction of metal chelates with DNA. 2. Tris-chelated complexes of cobalt (III) and iron (II) with 1, 10-phenanthroline and 2, 2'-bipyridine. Journal of the American Chemical Society 111.24 (1989): 8901-8911.

Cheng, et al. Development of an electrochemical membrane-based nanobiosensor for ultrasensitive detection of dengue virus. Anal Chim Acta. May 6, 2012;725:74-80. doi: 10.1016/j.aca.2012.03.017. Epub Mar. 17, 2012.

European search report and opinion dated Apr. 8, 2016 for EP Application No. 13879507.5.

Gonzalez, et al. Mass transport effect of mesoscopic domains in the amperometric response of an electroactive species: Modeling for its applications in biomolecule detection. Sensors and Actuators B: Chemical 144.2 (2010): 349-353.

He, et al. Gate manipulation of DNA capture into nanopores. ACS Nano. Oct. 25, 2011;5(10):8391-7. doi: 10.1021/nn203186c. Epub Sep. 26, 2011.

He, et al. Thermophoretic manipulation of DNA translocation through nanopores. ACS Nano. Jan. 22, 2013;7(1):538-46. doi: 10.1021/nn304914j. Epub Dec. 10, 2012.

Lee, et al. Surface charge study on pollen with a simple microelectrophoresis instrumentation setup. Biomedical Engineering and Sciences (IECBES), 2010 IEEE EMBS Conference on. Kuala Lumpur, Malaysia, Nov. 30-Oct. 2, 2010, pp. 364-368.

Office action dated May 25, 2016 for U.S. Appl. No. 14/421,809.

Office action dated Jun. 23, 2016 for U.S. Appl. No. 14/111,352.

Smith, et al. Electrophoretic distributions of human peripheral blood mononuclear white cells from normal subjects and from patients with acute lymphocytic leukemia Proc Natl Acad Sci U S A. Jul. 1976;73(7):2388-91.

Tsutsui, et al. Transverse electric field dragging of DNA in a nanochannel. Sci Rep. 2012;2:394. doi: 10.1038/srep00394. Epub May 3, 2012.

Woolley, et al. Capillary electrophoresis chips with integrated electrochemical detection.. Analytical Chemistry 70.4 (1998): 684-688.

U.S. Appl. No. 15/048,810, filed Feb. 19, 2016, Ikeda et al.
U.S. Appl. No. 15/048,889, filed Feb. 19, 2016, Kawai et al.
U.S. Appl. No. 15/061,871, filed Mar. 4, 2016, Kawai et al.
U.S. Appl. No. 15/098,147, filed Apr. 13, 2016, Ikeda et al.
Office action dated Feb. 5, 2016 for U.S. Appl. No. 14/112,189.
Office action dated Aug. 1, 2016 for U.S. Appl. No. 14/112,189.

Qiu, et al. Detecting ssDNA at single-nucleotide resolution by sub-2-nanometer pore in monoatomic graphene: A molecular dynamics study. Applied Physics Letters 100.8 (2012): 083106. 4 pages.

Zhao, et al. Single-strand DNA molecule translocation through nanoelectrode gaps. Nanotechnology. Oct. 24, 2007;18(42):424018. doi: 10.1088/0957-4484/18/42/424018. Epub Sep. 19, 2007. 7 pages.

Office action dated Aug. 26, 2016 for U.S. Appl. No. 14/687,856.
Office action dated Sep. 9, 2016 for U.S. Appl. No. 15/061,871.
Notice of allowance dated Sep. 15, 2016 for U.S. Appl. No. 14/421,809.
Office action dated Oct. 6, 2016 for U.S. Appl. No. 14/883,494.

* cited by examiner

METHOD FOR CONTROLLING SUBSTANCE MOVING SPEED AND APPARATUS FOR CONTROLLING THE SAME

CROSS-REFERENCE TO RELATED APPLICATION

This application is based upon and claims the benefit of priority of Japanese Patent Application No. 2012-286115, filed on Dec. 27, 2012, the entire contents of which are incorporated herein by reference.

BACKGROUND

1. Technical Field

The present invention relates to a method for controlling substance moving speed and apparatus for controlling the same.

2. Related Art

In recent years, tailor-made medicines adapted to individual differences have been garnering attention. In order to realize such tailor-made medicines, it is necessary to precisely decode the base sequences of individual genomes in a short amount of time and accurately understand features in the base sequences of the individual genomes.

Conventionally, the technique of electrophoresing, in a device in which a membrane protein is carried on a lipid bilayer membrane, a nucleic acid so that it passes between a pair of electrodes to thereby decode the base sequence of the nucleic acid has been used (e.g., see non-patent document 1: Clarke, J., Wu, H.-C., Jayasinghe, L., Patel, A., Reid, S. & Bayley, H., "Continuous base identification for single-molecule nanopore DNA sequencing," *Nature Nanotechnology* 4, 265-270 (2009)). Specifically, in the technique described in non-patent document 1, the nucleic acid is electrophoresed so that it passes through a hole formed by α-haemolysin in an electrolytic solution, and an ion current at this time is measured, whereby the base sequence of the nucleic acid passing through the hole is determined.

Sequencers for decoding the base sequences of nucleic acids such as described above decode the base sequence of a nucleic acid while causing the nucleic acid to move. At this time, if the moving speed of the nucleic acid is too fast, the sequencer cannot precisely determine the base sequence of the nucleic acid. On the other hand, if the moving speed of the nucleic acid is too slow, the sequencer requires an extremely large amount of time to decode the base sequence of the nucleic acid. Therefore, in the field of sequencers, for example, the development of a technology that can precisely control the moving speed of a substance to a desired speed is needed.

In view of this situation, conventionally, technologies that use the Coulomb force to decelerate the moving speed of nucleic acids have been disclosed (e.g., see non-patent document 2: Pei-chun Yen et al., *Review of Scientific Instruments,* 83, 034301 (2012)).

However, these conventional technologies have the problem that it is difficult for them to adjust the moving speed of a substance to a desired speed.

For example, there is the problem that if one tries to adjust the moving speed of a substance on the basis of the Coulomb force, basically the moving speed of the substance can only be decelerated, and the moving speed of the substance cannot be accelerated.

Further, if one tries to adjust the moving speed of a substance on the basis of the Coulomb force, the substance adheres around electrodes that are for causing the Coulomb force to act on the substance. Additionally, there is the problem that the motion of the substance whose moving speed one wants to adjust is hindered by the substance adhering around the electrodes.

SUMMARY OF THE INVENTION

One aspect of a method of controlling the moving speed of a substance of the present invention includes the steps of: causing a substance to move along an electric field formed by an electrode pair; and causing the substance to pass through an internal space of a surround electrode formed so as to surround part of the moving path of the substance to thereby change the moving speed of the substance, wherein the surround electrode is charged only to either one of positive or negative, and a medium having an electrolyte dissolved therein is disposed in the internal space of the surround electrode.

According to this configuration, the surround electrode is charged only to either one of positive or negative, so that either negative ions or positive ions derived from the electrolyte become attracted to the surface of the surround electrode at the side of the internal space. More specifically, in a case where the surround electrode is positively charged, negative ions become attracted to the surface of the surround electrode, and in a case where the surround electrode is negatively charged, positive ions become attracted to the surface of the surround electrode.

The negative ions or the positive ions that have become attracted to the surface of the surround electrode move to the side of the positive electrode or the negative electrode forming the electrode pair. That is, the negative ions that have become attracted to the surface of the surround electrode generate an electro-osmotic flow that moves to the side of the positive electrode of the electrode pair along the electric field formed by the electrode pair. On the other hand, the positive ions that have become attracted to the surface of the surround electrode generate an electro-osmotic flow that moves to the side of the negative electrode of the electrode pair along the electric field formed by the electrode pair.

The substance moves along the electric field formed by the electrode pair, so the moving direction of the substance and the direction of the electro-osmotic flow become substantially the same direction or substantially opposite directions. Additionally, in a case where both are substantially the same direction, the moving speed of the substance is accelerated, and in a case where both are substantially opposite directions, the moving speed of the substance is decelerated.

According to this configuration, the moving speed of the substance can be accelerated and can be decelerated as described above.

In the control method of the present invention, it is preferred that the substance be a substance that has a charge.

According to this configuration, the substance can be moved by the electrode pair without requiring a special configuration. For example, if the substance has a negative charge, the substance can be moved toward the positive electrode of the electrode pair. On the other hand, if the substance has a positive charge, the substance can be moved toward the negative electrode of the electrode pair.

In the control method of the present invention, it is preferred that a gate voltage of from −3 V to 3 V be applied to the surround electrode.

According to this configuration, a stronger electro-osmotic flow can be generated, so that the moving speed of the substance can be more reliably and more accurately controlled.

In the control method of the present invention, it is preferred that, when Y denotes the maximum width of the cross section, in a direction perpendicular to the moving direction of the substance, of the internal space of the surround electrode and X denotes the maximum width of the cross section, in a direction perpendicular to the moving direction of the substance, of the substance passing through the internal space of the surround electrode, a ratio R=X/Y (dimensionless) between the lengths of X and Y satisfies the relationship $0.5<X/Y<1$.

A stronger electro-osmotic flow is generated the closer it is to the surface of the surround electrode. According to this configuration, at least part of the substance is disposed near the surface of the surround electrode, so that the substance can be more reliably subjected to the force of the electro-osmotic flow. As a result, the moving speed of the substance can be more reliably and more accurately controlled. Further, according to this configuration, plural pieces of the substance (e.g., two molecules of DNA) can be prevented from entering the internal space of the surround electrode, so the moving speed of one piece (e.g., one molecule of DNA) of the substance can be controlled.

In the control method of the present invention, it is preferred that an electro-osmotic flow be generated in the internal space of the surround electrode.

According to this configuration, the moving speed of the substance can be better controlled.

In the control method of the present invention, it is preferred that the surround electrode be an electrode formed by a metal.

When a metal is used as the surround electrode, the moving speed of the substance can be linearly controlled. Conventional gate electrodes (e.g., see non-patent document 2) are made of semiconductors (silicon), so that changes in the electro-osmotic flow with respect to the gate voltage are nonlinear, but with a gate electrode using a metal electrode, there is a linear response, so that it is easy to control the moving speed of the substance.

One aspect of a apparatus for controlling substance moving speed of the present invention includes: a flow channel that is disposed between a pair of electrodes and that is for a substance to move through; and a surround electrode that is formed so as to surround part of the flow channel and changes the moving speed of the substance in the flow channel within an internal space of the surround electrode, wherein the surround electrode is charged only to either one of positive or negative, and a medium having an electrolyte dissolved therein is disposed in the internal space of the surround electrode.

According to this configuration, the surround electrode is charged only to either one of positive or negative, so that either negative ions or positive ions derived from the electrolyte become attracted to the surface of the surround electrode on the side of the internal space. More specifically, in a case where the surround electrode is positively charged, negative ions become attracted to the surface of the surround electrode, and in a case where the surround electrode is negatively charged, positive ions become attracted to the surface of the surround electrode.

The negative ions or the positive ions that have become attracted to the surface of the surround electrode move to the side of the positive electrode or the negative electrode forming the electrode pair. That is, the negative ions that have become attracted to the surface of the surround electrode generate an electro-osmotic flow that moves to the side of the positive electrode of the electrode pair along the electric field formed by the electrode pair. On the other hand, the positive ions that have become attracted to the surface of the surround electrode generate an electro-osmotic flow that moves to the side of the negative electrode of the electrode pair along the electric field formed by the electrode pair.

The substance moves along the flow channel disposed between the electrodes of the electrode pair (in other words, along the electric field formed by the electrode pair), so the moving direction of the substance and the direction of the electro-osmotic flow become substantially the same direction or substantially opposite directions. Additionally, in a case where both are substantially the same direction, the moving speed of the substance is accelerated, and in a case where both are substantially opposite directions, the moving speed of the substance is decelerated.

According to this configuration, the moving speed of the substance can be accelerated and can be decelerated as described above.

In the control apparatus of the present invention, it is preferred that the substance be a substance that has a charge.

According to this configuration, the substance can be moved by the electrode pair without requiring a special configuration. For example, if the substance has a negative charge, the substance can be moved toward the positive electrode of the electrode pair. On the other hand, if the substance has a positive charge, the substance can be moved toward the negative electrode of the electrode pair.

In the control apparatus of the present invention, it is preferred that a gate voltage of from −3 V to 3 V be applied to the surround electrode.

According to this configuration, a stronger electro-osmotic flow can be generated, so that the moving speed of the substance can be more reliably and more accurately controlled.

In the control apparatus of the present invention, it is preferred that, when Y denotes the maximum width of the cross section, in a direction perpendicular to the moving direction of the substance, of the internal space of the surround electrode and X denotes the maximum width of the cross section, in a direction perpendicular to the moving direction of the substance, of the substance passing through the internal space of the surround electrode, a ratio R=X/Y (dimensionless) between the lengths of X and Y satisfies the relationship $0.5<X/Y<1$.

A stronger electro-osmotic flow is generated the closer it is to the surface of the surround electrode. According to this configuration, at least part of the substance is disposed near the surface of the surround electrode, so that the substance can be more reliably subjected to the force of the electro-osmotic flow. As a result, the moving speed of the substance can be more reliably and more accurately controlled. Further, according to this configuration, plural pieces of the substance (e.g., two molecules of DNA) can be prevented from entering the internal space of the surround electrode, so that the moving speed of one piece (e.g., one molecule of DNA) of the substance can be controlled.

In the control apparatus of the present invention, it is preferred that the surround electrode generate an electro-osmotic flow in the flow channel within the internal space of the surround electrode.

According to this configuration, the moving speed of the substance can be better controlled.

In the control apparatus of the present invention, it is preferred that the surround electrode be an electrode formed by a metal.

When a metal is used as the surround electrode, the moving speed of the substance can be linearly controlled. Conventional gate electrodes (e.g., see non-patent document 2) are made of semiconductors (silicon), so that changes in the electro-osmotic flow with respect to the gate voltage are nonlinear, but with a gate electrode using a metal electrode, there is a linear response, so that it is easy to control the moving speed of the substance.

One aspect of a apparatus for determining the nucleotide sequences of polynucleotides of the present invention includes the control apparatus of the present invention.

According to this configuration, the nucleotide sequence of a polynucleotide can be determined after the moving speed of the polynucleotide has been adjusted to a desired speed, so that the nucleotide sequence can be accurately and rapidly determined.

The present invention can control the moving speed of a substance to a desired speed, so that it achieves the effect that various measurements relating to that substance can be rapidly and precisely performed. For example, to take the decoding of the base sequence of a nucleic acid as an example, by using the present invention to decelerate the moving speed of the nucleic acid, signals (e.g., current signals, fluorescence signals) detected for each base configuring the nucleic acid can be prevented from becoming superimposed, so that the base sequence of the nucleic acid can be precisely determined. Conversely, by using the present invention to accelerate the moving speed of the nucleic acid, the base sequence of the nucleic acid can be rapidly determined.

The present invention can, in the process of the substance moving, decelerate the substance only during a desired period and accelerate the substance during the remaining period by changing the voltage applied to the surround electrode. For example, the present invention can decelerate the substance only during a period in which some kind of measurement is to be performed with respect to the substance and accelerate the substance during other periods. Because this control can be performed, not only can an accurate measurement be performed, but also the total amount of time for the measurement can be shortened.

The present invention can adjust (form) the size of the internal space of the surround electrode (in other words, the width of the internal space of the surround electrode) to a desired size in accordance with the size of the substance. That is, the present invention can adjust (form) the size of the internal space of the surround electrode so that only one molecule of the substance can enter, whereby the present invention can accurately adjust the moving speed of one molecule of the substance.

DETAILED DESCRIPTION OF THE INVENTION

An embodiment of the present invention will be described below, but the present invention is not limited thereto. The present invention is capable of various changes in the scope described in the claims, and embodiments and working examples obtained by appropriately combining the technical means disclosed in different embodiments and working examples are also included in the technical scope of the present invention.

[1. Principle of Present Invention]

Figure 1A:
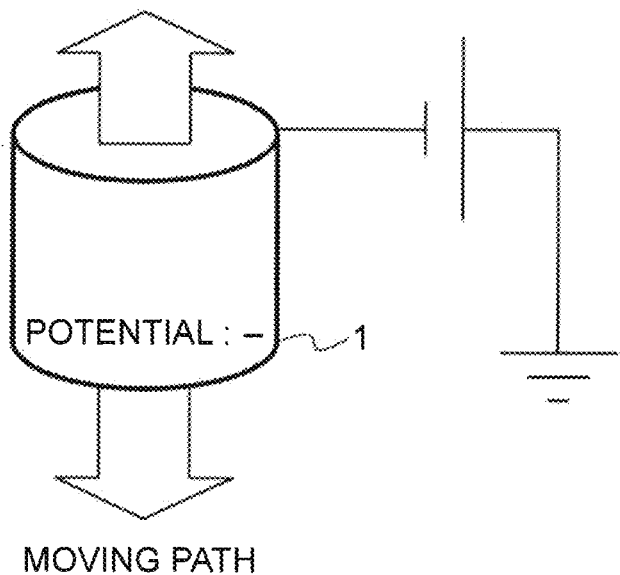
FIG. 1A is a drawing showing an embodiment of a surround electrode of the present invention.
Figure 1B:
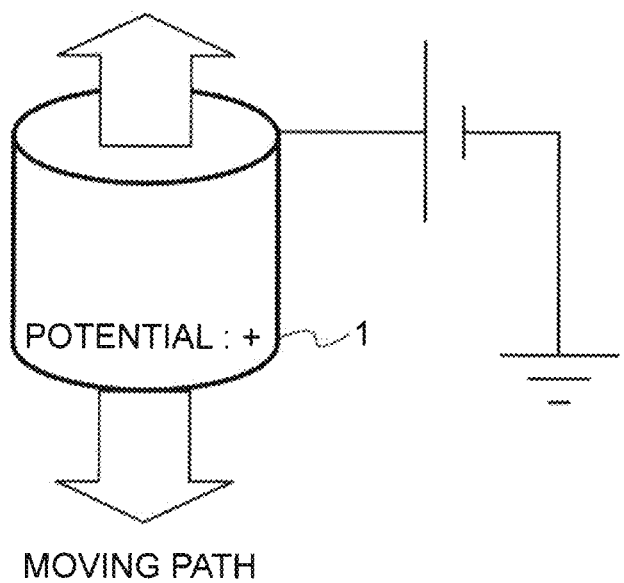
FIG. 1B is a drawing showing the embodiment of the surround electrode of the present invention.

First, a surround electrode 1 will be described using FIG. 1A and FIG. 1B.

The surround electrode 1 is an electrode formed surrounding part of a moving path of a substance (in other words, a flow channel).

The surround electrode 1 is formed as a single electrode, and substantially the same potential is applied to the entire surround electrode 1. For example, sometimes a positive potential is applied to the entire surround electrode 1 and sometimes a negative potential is applied to the entire surround electrode 1.

If the surround electrode 1 were formed as an opposing electrode pair comprising two electrodes, electro-osmotic flows heading in opposite directions would be generated on the surface of each electrode. That is, electro-osmotic flows heading in opposite directions would be generated in the internal space of the surround electrode 1. In this case, the electro-osmotic flows would cancel each other out and it would become difficult to effectively accelerate or decelerate the substance.

In contrast, in the present invention, substantially the same potential is applied to the entire surround electrode 1, so the direction of the electro-osmotic flow generated in the internal space of the surround electrode 1 can be aligned to one direction. Therefore, according to the present invention, it becomes possible to effectively accelerate or decelerate the substance.

Next, the principle of the present invention will be described using FIG. 2 and FIG. 3.

Figure 2:
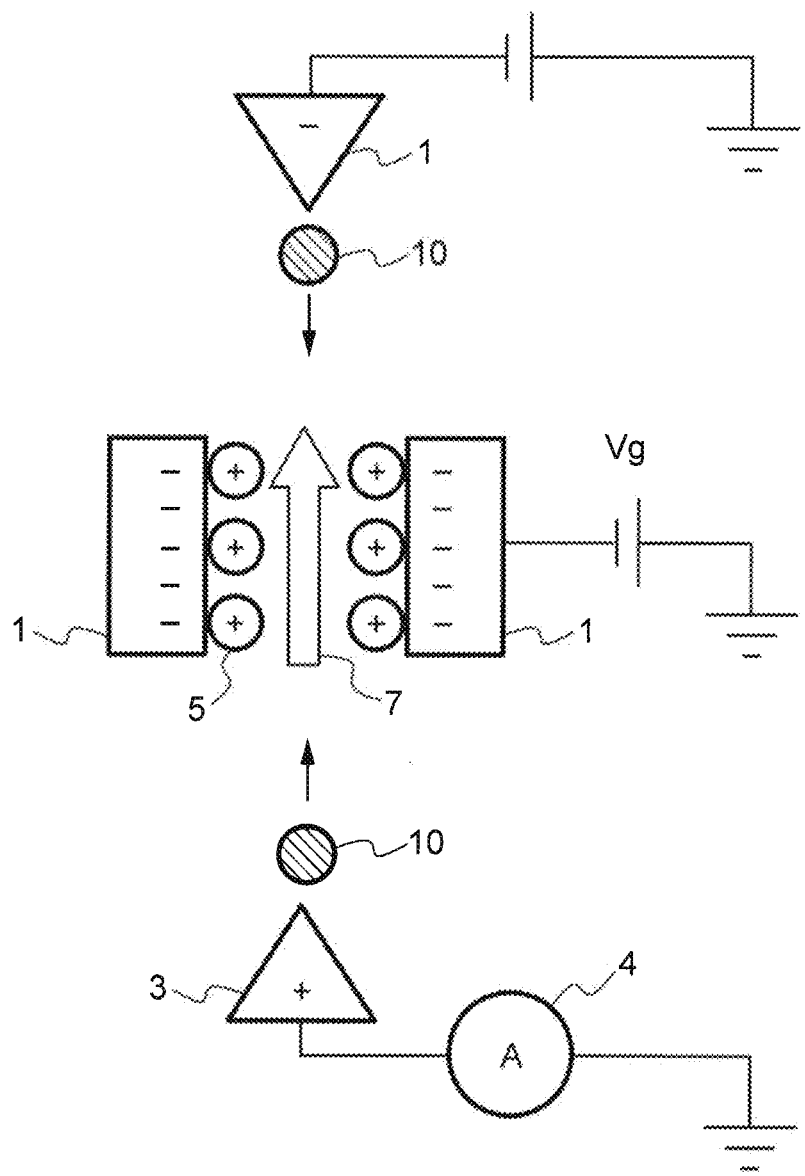
FIG. 2 is a drawing showing the principle of the present invention.

In the example shown in FIG. 2, a substance 10 is caused to move along a electric field formed by an electrode pair comprising a negative electrode 2 and a positive electrode 3. At this time, the substance 10 may move from the side of the negative electrode 2 toward the side of the positive electrode 3 or may move from the side of the positive electrode 3 toward the negative electrode 2.

For example, if a negatively charged substance is used as the substance 10, the substance 10 moves from the side of the negative electrode 2 toward the side of the positive electrode 3. On the other hand, if a positively charged substance is used as the substance 10, the substance 10 moves from the side of the positive electrode 3 toward the side of the negative electrode 2.

Of course, in the present invention, it is also possible to use an uncharged substance 10. In this case, the substance 10 may be moved by means other than the electrode pair comprising the negative electrode 2 and the positive electrode 3. For example, it is possible to cause the substance 10 to move by applying pressure to the substance 10 (or a medium existing between the negative electrode 2 and the positive electrode 3) using a well-known pump, and it is possible to cause the substance 10 to move by Brownian motion, but the present invention is not limited to these.

In the example shown in FIG. 2, the surround electrode 1 is disposed on the moving path of the substance 10, and the substance 10 passes through the internal space of the surround electrode 1.

The surround electrode 1 shown in FIG. 2 corresponds to a longitudinal section of the surround electrode 1 shown in FIG. 1. That is, the two sections of the surround electrode 1 shown in FIG. 2 represent different sections that substantially oppose one another in the single surround electrode 1. In the example shown in FIG. 2, a gate voltage Vg is applied to the surround electrode 1 to thereby negatively charge the surround electrode 1.

A medium having an electrolyte dissolved therein (e.g., an aqueous solution having an electrolyte dissolved therein) is disposed in the internal space in the surround electrode 1. As described above, the surround electrode 1 is negatively charged, so positive ions 5 in the medium become attracted to the surface of the surround electrode 1.

In accordance with the positional relationship between the negative electrode 2 and the positive electrode 3, an electro-osmotic flow 7 is generated by the positive ions 5 that have become attracted to the surround electrode 1, and the direction in which the electro-osmotic flow 7 flows is determined. That is, the electro-osmotic flow 7 flows from the side of the positive electrode 3 toward the side of the negative electrode 2. Additionally, the moving speed of the substance 10 becomes accelerated or decelerated in accordance with the direction in which the electro-osmotic flow 7 flows.

For example, in a case where, in FIG. 2, the substance 10 is moving from the side of the negative electrode 2 to the side of the positive electrode 3, the moving direction of the substance 10 and the direction of the electro-osmotic flow 7 are opposite, so the moving speed of the substance 10 becomes decelerated. On the other hand, in a case where, in FIG. 2, the substance 10 is moving from the side of the positive electrode 3 to the side of the negative electrode 2, the moving direction of the substance 10 and the direction of the electro-osmotic flow 7 are the same, so the moving speed of the substance 10 becomes accelerated.

Figure 3:
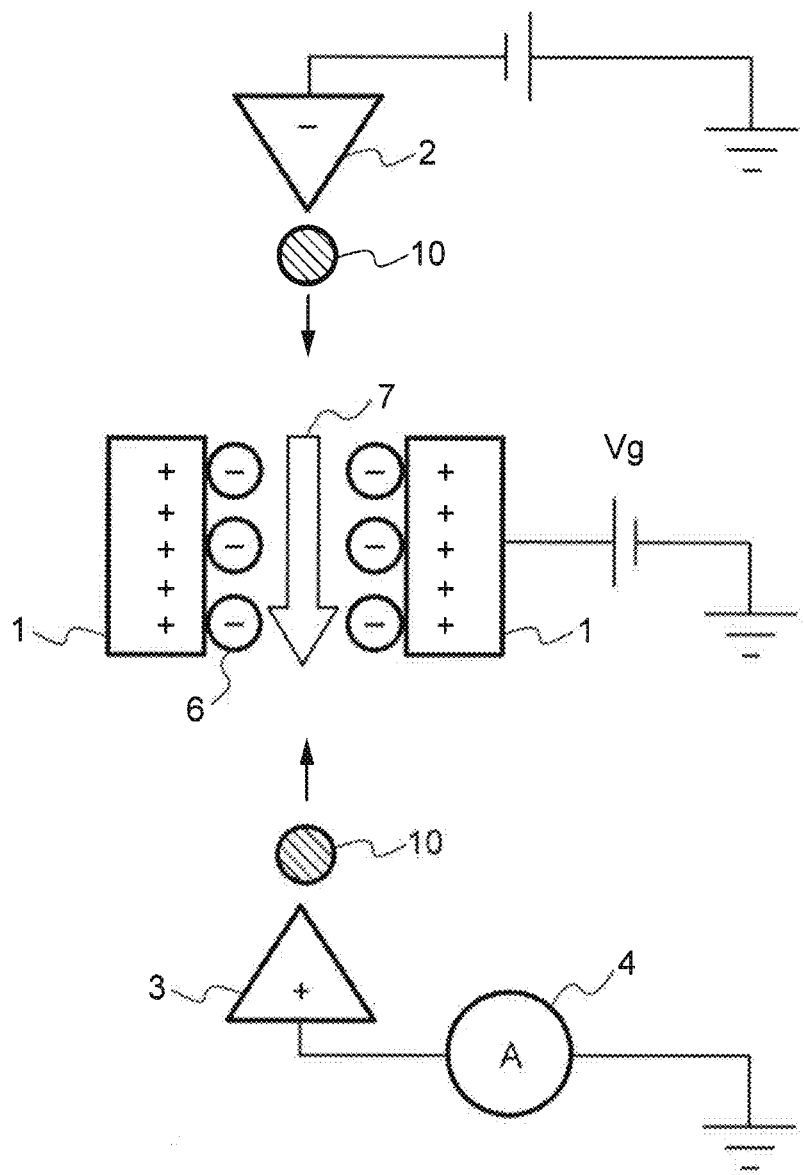
FIG. 3 is a drawing showing the principle of the present invention.

In the example shown in FIG. 3, a substance 10 is caused to move along an electric field formed by an electrode pair comprising a negative electrode 2 and a positive electrode 3. At this time, the substance 10 may move from the side of the negative electrode 2 toward the side of the positive electrode 3 or may move from the side of the positive electrode 3 toward the negative electrode 2.

For example, if a negatively charged substance is used as the substance 10, the substance 10 moves from the side of the negative electrode 2 toward the side of the positive electrode 3. On the other hand, if a positively charged substance is used as the substance 10, the substance 10 moves from the side of the positive electrode 3 toward the side of the negative electrode 2.

Of course, in the present invention, it is also possible to use an uncharged substance 10. In this case, the substance 10 may be moved by means other than the electrode pair comprising the negative electrode 2 and the positive electrode 3. For example, it is possible to cause the substance 10 to move by applying pressure to the substance 10 (or a medium existing between the negative electrode 2 and the positive electrode 3) using a well-known pump, and it is possible to cause the substance 10 to move by Brownian motion, but the present invention is not limited to these.

In the example shown in FIG. 3, the surround electrode 1 is disposed on the moving path of the substance 10, and the substance 10 passes through the internal space of the surround electrode 1.

The surround electrode 1 shown in FIG. 3 corresponds to a longitudinal section of the surround electrode 1 shown in FIG. 1. That is, the two sections of the surround electrode 1 shown in FIG. 3 represent different sections that substantially oppose one another in the single surround electrode 1. In the example shown in FIG. 3, a gate voltage Vg is applied to the surround electrode 1 to thereby positively charge the surround electrode 1.

A medium having an electrolyte dissolved therein (e.g., an aqueous solution having an electrolyte dissolved therein) is disposed in the internal space in the surround electrode 1. As described above, the surround electrode 1 is positively charged, so negative ions 6 in the medium become attracted to the surface of the surround electrode 1.

In accordance with the positional relationship between the negative electrode 2 and the positive electrode 3, an electro-osmotic flow 7 is generated by the negative ions 6 that have become attracted to the surround electrode 1, and the direction in which the electro-osmotic flow 7 flows is determined. That is, the electro-osmotic flow 7 flows from the side of the negative electrode 2 toward the side of the positive electrode 3. Additionally, the moving speed of the substance 10 becomes accelerated or decelerated in accordance with the direction in which the electro-osmotic flow 7 flows.

For example, in a case where, in FIG. 3, the substance 10 is moving from the side of the negative electrode 2 to the side of the positive electrode 3, the moving direction of the substance 10 and the direction of the electro-osmotic flow 7 are the same, so the moving speed of the substance 10 becomes accelerated. On the other hand, in a case where, in FIG. 3, the substance 10 is moving from the side of the positive electrode 3 to the side of the negative electrode 2, the moving direction of the substance 10 and the direction of the electro-osmotic flow 7 are opposite, so the moving speed of the substance 10 becomes decelerated.

[2. Method of Controlling Moving Speed of Substance]

A control method of the present embodiment has a moving step of causing a substance to move along an electric field formed by an electrode pair. By causing the substance to move along the electric field formed by the electrode pair, the moving direction of the substance and the direction of the electro-osmotic flow can be made substantially the same direction or substantially opposite directions. Additionally, the moving speed of the substance can be accelerated by making the moving direction of the substance and the direction of the electro-osmotic flow substantially the same direction, and the moving speed of the substance can be decelerated by making the moving direction of the substance and the direction of the electro-osmotic flow substantially opposite directions.

It is not necessary for the direction of the electric field formed by the electrode pair and the moving direction of the substance to be completely parallel. That is, the direction of the electric field formed by the electrode pair and the moving direction of the substance may also be divergent. For example, the divergence between the direction of the electric field formed by the electrode pair and the moving direction of the substance (in other words, the smaller angle of the angles formed by the intersection of a line along the electric field formed by the electrode pair and a line along the moving direction of the substance) is preferably equal to or greater than 0° and less than 90°, more preferably equal to or greater than 0° and equal to or less than 80°, more preferably equal to or greater than 0° and equal to or less than 70°, more preferably equal to or greater than 0° and equal to or less than 60°, more preferably equal to or greater than 0° and equal to or less than 50°, more preferably equal to or greater than 0° and equal to or less than 45°, more preferably equal to or greater than 0° and equal to or less than 40°, more preferably equal to or greater than 0° and equal to or less than 30°, more preferably equal to or greater than 0° and equal to or less than 20°, more preferably equal to or greater than 0° and equal to or less than 10°, more preferably equal to or greater than 0° and equal to or less than 5°, and most preferably 0°.

If the angle is equal to or greater than 0° and equal to or less than 45°, the divergence between the direction of the electric field formed by the electrode pair and the moving direction of the substance is small, so the moving speed of the substance can be more effectively controlled.

The substance is not particularly limited, and it is possible to use an appropriate desired substance. Examples of the substance can be broadly divided into substances that have a charge and substances that do not have a charge.

In the case of using a substance that has a charge as the substance, in the moving step, the substance can be moved by the electrical interaction between the electrodes of the electrode pair. For example, in the case of using a substance that has a negative charge as the substance, the substance moves from the negative electrode side toward the positive electrode side of the electrode pair. On the other hand, in the case of using a substance that has a positive charge as the substance, the substance moves from the positive electrode side toward the negative electrode side of the electrode pair.

In the case of using a substance that does not have a charge as the substance, in the moving step, the substance is moved using a configuration other than an electrode pair. For example, it is possible to cause the substance to move using a well-known pump, and it is possible to cause the substance to move by Brownian motion.

Regardless of whether the substance has been moved by electrical interaction or whether the substance has been moved by physical force, the moving speed of the substance can be accelerated by making the moving direction of the substance and the direction of the electro-osmotic flow substantially the same direction, and the moving speed of the substance can be decelerated by making the moving direction of the substance and the direction of the electro-osmotic flow substantially opposite directions.

The substance is not particularly limited and may, for example, be an atom, a molecule, a polymer, or a complex of these. More specifically, examples of the substance can include a nucleic acid (DNA or RNA), an amino acid, a protein, a pollen grain, a virus, a fungal cell, a cell, an organic particle, or an inorganic particle.

As described above, the substance may be a complex. For example, in a case where the substance is a complex of a substance A and a substance B, at least one of the substance A and the substance B may have a charge, or both the substance A and the substance B may have a charge, or both the substance A and the substance B may not have a charge.

In a case where both the substance A and the substance B have a charge, the charge that the substance A has and the charge that the substance B has may both be positive or negative charges, or one may be a positive charge and the other may be a negative charge.

In a case where one of the charge that the substance A has and the charge that the substance B has is a positive charge and the other is a negative charge, when the complex is seen as a whole, the complex may have a charge or the charges may cancel one another so that the complex does not have a charge.

In a case where the substance is a complex of a substance A and a substance B, the substance A and the substance B may be bonded to one another by a force to the extent that they do not separate from one another while moving. For example, the substance A and the substance B may be bonded to one another via a covalent bond, an ionic bond, a hydrogen bond, a hydrophobic bond, or plural bonds selected from these.

For example, by using an ionic surfactant (e.g., sodium dodecyl sulfate) as the substance A and causing the substance B to be included in a micelle formed by the substance A, a charge can be imparted to the desired substance B. Additionally, the complex can be easily moved by the electrical interaction between the electrodes of the electrode pair.

The moving step includes the step of causing the substance to pass through an internal space, in which an electro-osmotic flow is generated, of a surround electrode formed surrounding part of the moving path of the substance. Additionally, the surround electrode is charged only to either one of positive or negative, and a medium having an electrolyte dissolved therein is disposed in the internal space of the surround electrode.

Because the surround electrode is charged only to either one of positive or negative, only either one of negative ions or positive ions derived from the electrolyte can be attracted to the surface facing the internal space of the surround electrode. Additionally, because the electro-osmotic flow is generated by only either one of negative ions or positive ions, the direction in which the electro-osmotic flow flows can be aligned. Additionally, because the direction in which the electro-osmotic flow flows can be aligned, the moving speed of the substance can be accurately controlled by the electro-osmotic flow.

The method for charging the surround electrode to either one of positive or negative is not particularly limited. For example, well-known voltage applying means may be used to apply a desired gate voltage to the surround electrode.

The voltage applied to the surround electrode is not particularly limited and may, for example, be equal to or greater than −5 V and equal to or less than 5 V, or equal to or greater than −3 V and equal to or less than 3 V, or equal to or greater than −1 V and equal to or less than 1 V.

In the case of applying a negative gate voltage to the surround electrode, the value of the gate voltage to be applied is not particularly limited and is, for example, preferably equal to or less than −0.1 V, more preferably equal to or less than −0.2 V, more preferably equal to or less than −0.3 V, more preferably equal to or less than −0.4 V, more preferably equal to or less than −0.5 V, and most preferably equal to or less than −1.0 V.

By applying a gate voltage equal to or less than −0.5 V to the surround electrode, a strong electro-osmotic flow can be generated, so the moving speed of the substance can be reliably and accurately controlled. Further, by applying a gate voltage equal to or less than −1.0 V to the surround electrode, a stronger electro-osmotic flow can be generated, so the substance can be better decelerated or accelerated compared to the case of applying a gate voltage of −0.5 V.

On the other hand, in the case of applying a positive gate voltage to the surround electrode, the value of the gate voltage to be applied is not particularly limited and is, for example, preferably equal to or greater than 0.1 V, more preferably equal to or greater than 0.2 V, more preferably equal to or greater than 0.25 V, more preferably equal to or greater than 0.5 V, and most preferably equal to or greater than 1.0 V.

By applying a gate voltage equal to or greater than 0.25 V to the surround electrode, a strong electro-osmotic flow can be generated, so the moving speed of the substance can be reliably and accurately controlled. Further, by applying a gate voltage equal to or greater than 0.5 V or equal to or greater than 1.0 V to the surround electrode, a stronger electro-osmotic flow can be generated, so the substance can be better decelerated or accelerated compared to the case of applying a gate voltage of 0.25 V.

The specific configuration of the surround electrode is not particularly limited and may, for example, comprise a substrate having a through hole formed therein, with the surface of the through hole being annularly or tubularly coated with a metal (e.g., a metal film) that functions as an electrode. Additionally, the annular or tubular metal can be caused to function as the surround electrode.

Using a metal as the surround electrode has the advantage that the moving speed of the substance can be linearly controlled. Conventional gate electrodes (e.g., see nonpatent document 2) are made of semiconductors (silicon), so changes in the electro-osmotic flow with respect to the gate voltage are nonlinear, but with a gate electrode using a metal electrode, there is a linear response, so it is easy to control the moving speed of the substance.

The metal is not particularly limited, and examples thereof can include Pt, Au, Cr, Ag, Al, and Cu. Further, it is also possible to form the surround electrode using plural metals. For example, it is possible to use "Pt/Au/Pt/Cr". In the case of forming the surround electrode using plural metals, the thickness of each metal layer is not particularly limited.

In the control method of the present embodiment, the substance passes through the internal space of the surround electrode in which the electro-osmotic flow is generated. The electro-osmotic flow is generated in the neighborhood of the surface of the surround electrode, so a stronger electro-osmotic flow is generated the closer it is to the surface of the surround electrode. Therefore, by adjusting the shape of the internal space of the surround electrode, it becomes possible to more effectively allow the electro-osmotic flow to act on the substance.

The shape of the internal space of the surround electrode is not particularly limited and is, for example, preferably tubular. In this case, the substance enters the inside of the tube from an opening on one end side of the tube, moves through the internal space of the tube, and exits to the outside of the tube from an opening on the other end side of the tube.

The shape of the cross section of the internal space in a direction perpendicular to the moving direction of the substance is not particularly limited and may, for example, be circular or polygonal (e.g., tetragonal, pentagonal, hexagonal, heptagonal, octagonal, etc.).

From the standpoints of more easily forming the internal space and generating an electro-osmotic flow whose flow is more stable, the shape of the cross section of the internal space in a direction perpendicular to the moving direction of the substance is preferably circular.

In the control method of the present embodiment, when Y denotes the maximum width of the cross section, in a direction perpendicular to the moving direction of the substance, of the internal space of the surround electrode and X denotes the maximum width of the cross section, in a direction perpendicular to the moving direction of the substance, of the substance passing through the internal space of the surround electrode, a ratio $R=X/Y$ (dimensionless) between the lengths of X and Y preferably satisfies the relationship of $0.50<X/Y<1$, more preferably satisfies the relationship of $0.60<X/Y<1$, more preferably satisfies the relationship of $0.65<X/Y<1$, more preferably satisfies the relationship of $0.70<X/Y<1$, more preferably satisfies the relationship of $0.80<X/Y<1$, more preferably satisfies the relationship of $0.90<X/Y<1$, and most preferably satisfies the relationship of $0.95<X/Y<1$.

According to this configuration, at least part of the substance is disposed near the surface of the surround electrode, so the substance can be more reliably subjected to the force of the electro-osmotic flow. As a result, the moving speed of the substance can be more reliably controlled. Further, according to this configuration, plural pieces of the substance (e.g., two molecules of DNA, etc.) can be prevented from entering the internal space of the surround electrode, so the moving speed of one piece (e.g., one molecule of DNA, etc.) of the substance can be controlled.

Figure 4A:
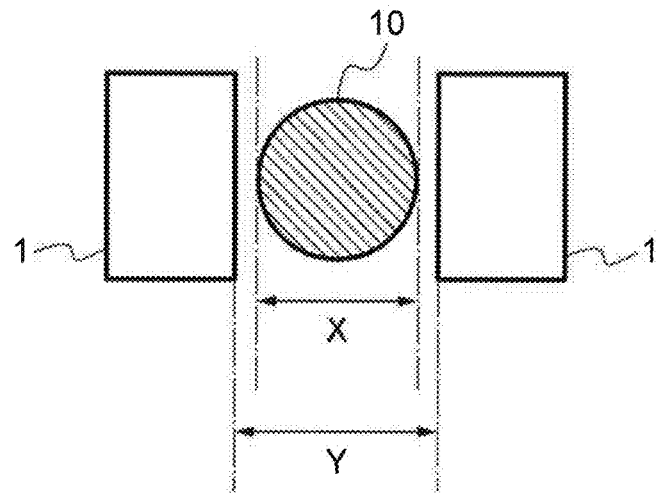
FIG. 4A is a drawing showing the state of a substance passing through an internal space of the surround electrode.

For example, let us consider a case where, as shown in FIG. 4A, a substantially spherical substance 10 (e.g., a particle, a pollen grain, a molecule, a fungal cell, etc.) passes through the internal space of the surround electrode 1.

At this time, as shown in FIG. 4A, when Y denotes the maximum width of the cross section, in a direction perpendicular to the moving direction of the substance 10, of the internal space of the surround electrode 1 and X denotes the maximum width of the cross section, in a direction perpendicular to the moving direction of the substance 10, of the substance 10 passing through the internal space of the surround electrode 1, if X and Y satisfy the relationship described above, then at least part of the substance 10 passes the neighborhood of the surface of the surround electrode 1. A stronger electro-osmotic flow is generated in the neighborhood of the surface of the surround electrode 1, so the substance 10 becomes more greatly subjected to the effect of that strong electro-osmotic flow. As a result, the moving speed of the substance 10 can be better controlled.

Figure 4B:
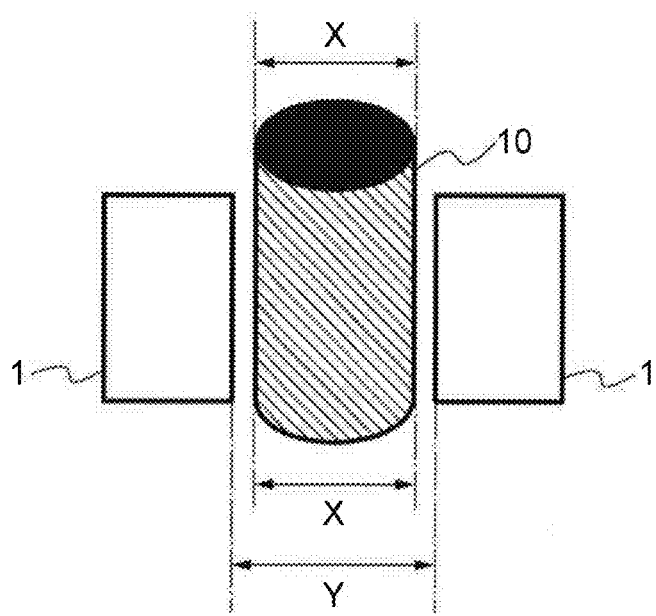
FIG. 4B is a drawing showing the state of the substance passing through the internal space of the surround electrode.

Further, let us consider a case where, as shown in FIG. 4B, a substantially cylindrical substance 10 (e.g., various polymers such as nucleic acids, nanorods, or *bacillus subtilis*, etc.) passes through the internal space of the surround electrode 1.

At this time, as shown in FIG. 4B, when Y denotes the maximum width of the cross section, in a direction perpendicular to the moving direction of the substance 10, of the internal space of the surround electrode 1 and X denotes the maximum width of the cross section, in a direction perpendicular to the moving direction of the substance 10, of the substance 10 passing through the internal space of the surround electrode 1, if X and Y satisfy the relationship described above, then at least part of the substance 10 passes the neighborhood of the surface of the surround electrode 1. A stronger electro-osmotic flow is generated in the neighborhood of the surface of the surround electrode 1, so the substance 10 becomes more greatly subjected to the effect of that strong electro-osmotic flow. As a result, the moving speed of the substance 10 can be better controlled.

In the control method of the present embodiment, the maximum width of the cross section, in a direction perpendicular to the moving direction of the substance, of the internal space of the surround electrode is preferably shorter than 1.2 μm, more preferably equal to or less than 1.0 μm, more preferably equal to or less than 0.85 μm, more preferably equal to or less than 0.35 μm, more preferably equal to or less than 0.20 μm, more preferably equal to or less than 0.15 μm, more preferably equal to or less than 0.04 μm, and more preferably equal to or less than 0.02 μm.

A stronger electro-osmotic flow is generated in the neighborhood of the surface of the surround electrode. Therefore, if one is trying to generate a strong electro-osmotic flow in the entire internal space of the surround electrode, the shorter the maximum width of the cross section, in a direction perpendicular to the moving direction of the substance, of the internal space of the surround electrode is, the more preferable.

When the maximum width of the cross section, in a direction perpendicular to the moving direction of the substance, of the internal space of the surround electrode is in the range described above, a strong electro-osmotic force can be generated in the entire internal space of the surround electrode, and thus the moving speed of the substance can be better controlled.

The medium having the electrolyte dissolved therein is disposed in the internal space of the surround electrode. The medium can also be disposed between the positive electrode and the negative electrode of the electrode pair described above.

The medium is not particularly limited, and, for example, a liquid, a gel, or a mixture of these can be used.

The liquid is not particularly limited, and examples thereof can include water, TE buffer (Tris-HCl, EDTA buffer), or an aqueous solution containing a chloride (e.g., KCl, LiCl, or NaCl). From the standpoint of generating a stronger electro-osmotic flow, among these, an aqueous solution containing KCl, whose ion mobility is high, is preferred. Further, the electro-osmotic flow becomes stronger the more the pH deviates from 7, so an electrolytic solution in which Tris-HCl and KCl or the like are mixed together is also preferred.

The gel is not particularly limited, and examples thereof can include polyacrylamide gel, agarose gel, dextran, or polyethylene glycol. From the standpoint of generating a stronger electro-osmotic flow, among these, low-viscosity dextran or polyethylene glycol is preferred.

The electrolyte dissolved in the medium is not particularly limited, and using KCl, NaCl, LiCl, or the like, for example, is preferred.

In the case of using KCl as the electrolyte, the concentration of the electrolyte in the medium is not particularly limited and, for example, is preferably equal to or greater than 1 mM and equal to or less than 1 M and more preferably equal to or greater than 100 mM and equal to or less than 1 M. According to this configuration, a stronger electro-osmotic flow can be generated.

In the case of using NaCl as the electrolyte, the concentration of the electrolyte in the medium is not particularly limited and, for example, is preferably equal to or greater than 1 mM and equal to or less than 1 M and more preferably equal to or greater than 100 mM and equal to or less than 1 M. According to this configuration, a stronger electro-osmotic flow can be generated.

In the case of using LiCl as the electrolyte, the concentration of the electrolyte in the medium is not particularly limited and, for example, is preferably equal to or greater than 1 mM and equal to or less than 1 M and more preferably equal to or greater than 100 mM and equal to or less than 1 M. According to this configuration, a stronger electro-osmotic flow can be generated.

In the control method of the present invention, the concentration of the electrolytic solution is preferably equal to or greater than 1 mM and equal to or less than 1 M, and the flow region (the Debye length) of the electro-osmotic flow can be controlled by changing the concentration. For example, the flow region (the Debye length) becomes narrower by increasing the concentration, and the flow region (the Debye length) becomes wider by decreasing the concentration.

[3. Apparatus for Controlling Substance Moving Speed]

A control apparatus of the present embodiment includes: a flow channel that is disposed between a pair of electrodes and is for a substance to move through; and a surround electrode that is formed surrounding part of the flow channel and generates an electro-osmotic flow in the flow channel placed in an internal space of the surround electrode to thereby change the moving speed of the substance.

The flow channel is preferably disposed extending along an electric field formed by the electrode pair. This configuration can cause the substance to move along the electric field formed by the electrode pair.

By causing the substance to move along the electric field formed by the electrode pair, the moving direction of the substance and the direction of the electro-osmotic flow can be made substantially the same direction or substantially opposite directions. Additionally, the moving speed of the substance can be accelerated by making the moving direction of the substance and the direction of the electro-osmotic flow substantially the same direction, and the moving speed of the substance can be decelerated by making the moving direction of the substance and the direction of the electro-osmotic flow substantially opposite directions.

It is not necessary for the direction of the electric field formed by the electrode pair and the direction in which the flow channel extends to be completely parallel. That is, the direction of the electric field formed by the electrode pair and the direction in which the flow channel extends may also be divergent. For example, the divergence between the direction of the electric field formed by the electrode pair and the direction in which the flow channel extends (in other words, the smaller angle of the angles formed by the intersection of a line along the electric field formed by the electrode pair and a line along the direction in which the flow channel extends) is preferably equal to or greater than 0° and less than 90°, more preferably equal to or greater than 0° and equal to or less than 80°, more preferably equal to or greater than 0° and equal to or less than 70°, more preferably equal to or greater than 0° and equal to or less than 60°, more preferably equal to or greater than 0° and equal to or less than 50°, more preferably equal to or greater than 0° and equal to or less than 45°, more preferably equal to or greater than 0° and equal to or less than 40°, more preferably equal to or greater than 0° and equal to or less than 30°, more preferably equal to or greater than 0° and equal to or less than 20°, more preferably equal to or greater than 0° and equal to or less than 10°, more preferably equal to or greater than 0° and equal to or less than 5°, and most preferably 0°.

If the angle is equal to or greater than 0° and equal to or less than 45°, the divergence between the direction of the electric field formed by the electrode pair and the direction in which the flow channel extends is small, so the moving speed of the substance can be more effectively controlled.

The length of the width of the flow channel (the width in a direction substantially perpendicular to the moving direction of the substance) is not particularly limited. The flow channel may have the same width across the entire flow channel or may have a width that is partially different. For example, the section of the flow channel surrounded by the surround electrode may be narrower compared to the other sections. In the control apparatus of the present embodiment, the entire internal space of the surround electrode described later can be used as part of the flow channel. That is, the flow channel in the control apparatus of the present embodiment may be formed by the region from the negative electrode of the electrode pair to the surround electrode, the internal space of the surround electrode, and the region from the positive electrode of the electrode pair to the surround electrode.

The surround electrode is formed surrounding part of the flow channel for the substance to move through. Additionally, the surround electrode is charged only to either one of positive or negative, and a medium having an electrolyte dissolved therein is disposed in the internal space of the surround electrode.

Because the surround electrode is charged only to either one of positive or negative, only either one of negative ions or positive ions derived from the electrolyte can be attracted to the surface facing the internal space of the surround electrode. Additionally, because the electro-osmotic flow is generated by only either one of negative ions or positive ions, the direction in which the electro-osmotic flow flows can be aligned. Additionally, because the direction in which the electro-osmotic flow flows can be aligned, the moving speed of the substance can be accurately controlled by the electro-osmotic flow.

The method for charging the surround electrode to either one of positive or negative is not particularly limited. For example, well-known voltage applying means may be used to apply a desired gate voltage to the surround electrode.

The voltage applied to the surround electrode is not particularly limited and may, for example, be equal to or greater than −5 V and equal to or less than 5 V, equal to or greater than −3 V and equal to or less than 3 V, or equal to or greater than −1 V and equal to or less than 1 V.

In the case of applying a negative gate voltage to the surround electrode, the value of the gate voltage to be applied is not particularly limited and is, for example, preferably equal to or less than −0.1 V, more preferably equal to or less than −0.2 V, more preferably equal to or less than −0.3 V, more preferably equal to or less than −0.4 V, more preferably equal to or less than −0.5 V, and most preferably equal to or less than −1.0 V.

By applying a gate voltage equal to or less than −0.5 V to the surround electrode, a strong electro-osmotic flow can be generated, so the moving speed of the substance can be reliably and accurately controlled. Further, by applying a gate voltage equal to or less than −1.0 V to the surround electrode, a stronger electro-osmotic flow can be generated, so the substance can be better decelerated or accelerated compared to the case of applying a gate voltage of −0.5 V.

On the other hand, in the case of applying a positive gate voltage to the surround electrode, the value of the gate voltage to be applied is not particularly limited and is, for example, preferably equal to or greater than 0.1 V, more preferably equal to or greater than 0.2 V, more preferably equal to or greater than 0.25 V, more preferably equal to or greater than 0.5 V, and most preferably equal to or greater than 1.0 V.

By applying a gate voltage equal to or greater than 0.25 V to the surround electrode, a strong electro-osmotic flow can be generated, so the moving speed of the substance can be reliably and accurately controlled. Further, by applying a gate voltage equal to or greater than 0.5 V or equal to or greater than 1.0 V to the surround electrode, a stronger electro-osmotic flow can be generated, so the substance can be better decelerated or accelerated compared to the case of applying a gate voltage of 0.25 V.

The specific configuration of the surround electrode is not particularly limited and may, for example, comprise a substrate having a through hole formed therein, with the surface of the through hole being annularly or tubularly coated with a metal (e.g., a metal film) that functions as an electrode. Additionally, the annular or tubular metal can be caused to function as the surround electrode.

Using a metal as the surround electrode has the advantage that the moving speed of the substance can be linearly controlled. Conventional gate electrodes (e.g., see non-patent document 2) are made of semiconductors (silicon), so changes in the electro-osmotic flow with respect to the gate voltage are nonlinear, but with a gate electrode using a metal electrode, there is a linear response, so it is easy to control the moving speed of the substance.

The metal is not particularly limited, and examples thereof can include Pt, Au, Cr, Ag, Al, and Cu. Further, it is also possible to form the surround electrode using plural metals. For example, it is also possible to use "Pt/Au/Pt/Cr". In the case of forming the surround electrode using plural metals, the thickness of each metal layer is not particularly limited.

In the control apparatus of the present embodiment, the flow channel (in other words, the substance) passes through the internal space of the surround electrode in which the electro-osmotic flow is generated. The electro-osmotic flow is generated in the neighborhood of the surface of the surround electrode, so a stronger electro-osmotic flow is generated the closer it is to the surface of the surround electrode. Therefore, by adjusting the shape of the internal space of the surround electrode, it becomes possible to more effectively allow the electro-osmotic flow to act on the substance.

The shape of the internal space of the surround electrode is not particularly limited and is, for example, preferably tubular. In this case, the substance enters the inside of the tube from an opening on one end side of the tube, moves through the internal space of the tube, and exits to the outside of the tube from an opening on the other end side of the tube.

The shape of the cross section of the internal space in a direction perpendicular to the moving direction of the substance is not particularly limited and may, for example, be circular or polygonal (e.g., tetragonal, pentagonal, hexagonal, heptagonal, octagonal, etc.).

From the standpoints of more easily forming the internal space and generating an electro-osmotic flow whose flow is more stable, the shape of the cross section of the internal space in a direction perpendicular to the moving direction of the substance is preferably circular.

In the control apparatus of the present embodiment, when Y denotes the maximum width of the cross section, in a direction perpendicular to the moving direction of the substance, of the internal space of the surround electrode and X denotes the maximum width of the cross section, in a direction perpendicular to the moving direction of the substance, of the substance passing through the internal space of the surround electrode, a ratio $R=X/Y$ (dimensionless) between the lengths of X and Y preferably satisfies the relationship of $0.50<X/Y<1$, more preferably satisfies the relationship of $0.60<X/Y<1$, more preferably satisfies the relationship of $0.65<X/Y<1$, more preferably satisfies the relationship of $0.70<X/Y<1$, more preferably satisfies the relationship of $0.80<X/Y<1$, more preferably satisfies the relationship of $0.90<X/Y<1$, and most preferably satisfies the relationship of $0.95<X/Y<1$.

According to this configuration, at least part of the substance is disposed near the surface of the surround electrode, so the substance can be more reliably subjected to the force of the electro-osmotic flow. As a result, the moving speed of the substance can be more reliably controlled. Further, according to this configuration, plural pieces of the substance (e.g., two molecules of DNA, etc.) can be prevented from entering the internal space of the surround electrode, so the moving speed of one piece (e.g., one molecule of DNA, etc.) of the substance can be controlled.

In the control apparatus of the present embodiment, the maximum width of the cross section, in a direction perpendicular to the moving direction of the substance, of the internal space of the surround electrode is preferably shorter than 1.2 μm, more preferably shorter than 1.0 μm, more preferably shorter than 0.85 μm, more preferably shorter than 0.35 μm, more preferably shorter than 0.20 μm, more preferably shorter than 0.15 μm, more preferably shorter than 0.04 μm, and more preferably shorter than 0.02 μm.

A stronger electro-osmotic flow is generated in the neighborhood of the surface of the surround electrode. Therefore, if one is trying to generate a strong electro-osmotic flow in the entire internal space of the surround electrode, the shorter the maximum width of the cross section, in a direction perpendicular to the moving direction of the substance, of the internal space of the surround electrode is, the more preferable.

When the maximum width of the cross section, in a direction perpendicular to the moving direction of the substance, of the internal space of the surround electrode is in the range described above, a strong electro-osmotic force can be generated in the entire internal space of the surround electrode, and thus the moving speed of the substance can be better controlled.

The medium having the electrolyte dissolved therein is disposed in the internal space of the surround electrode. The medium can also be disposed between the positive electrode and the negative electrode of the electrode pair described above.

The medium is not particularly limited, and, for example, a liquid, a gel, or a mixture of these can be used.

The liquid is not particularly limited, and examples thereof can include water, TE buffer (Tris-HCl, EDTA buffer), or an aqueous solution containing a chloride (e.g., KCl, LiCl, or NaCl). From the standpoint of generating a stronger electro-osmotic flow, among these, an aqueous solution containing KCl, whose ion mobility is high, is preferred. Further, the electro-osmotic flow becomes stronger the more the pH deviates from 7, so an electrolytic solution in which Tris-HCl and KCl or the like are mixed together is also preferred.

The gel is not particularly limited, and examples thereof can include polyacrylamide gel, agarose gel, dextran, and polyethylene glycol. From the standpoint of generating a stronger electro-osmotic flow, among these, low-viscosity dextran or polyethylene glycol is preferred.

The electrolyte dissolved in the medium is not particularly limited, and using KCl, NaCl, LiCl, or the like, for example, is preferred.

In the case of using KCl as the electrolyte, the concentration of the electrolyte in the medium is not particularly limited and, for example, is preferably equal to or greater than 1 mM and equal to or less than 1 M and more preferably equal to or greater than 100 mM and equal to or less than 1 M. According to this configuration, a stronger electro-osmotic flow can be generated.

In the case of using NaCl as the electrolyte, the concentration of the electrolyte in the medium is not particularly limited and, for example, is preferably equal to or greater than 1 mM and equal to or less than 1 M and more preferably equal to or greater than 100 mM and equal to or less than 1 M. According to this configuration, a stronger electro-osmotic flow can be generated.

In the case of using LiCl as the electrolyte, the concentration of the electrolyte in the medium is not particularly limited and, for example, is preferably equal to or greater than 1 mM and equal to or less than 1 M and more preferably equal to or greater than 100 mM and equal to or less than 1 M. According to this configuration, a stronger electro-osmotic flow can be generated.

In the control apparatus of the present invention, the concentration of the electrolytic solution is preferably equal to or greater than 1 mM and equal to or less than 1 M, and the flow region (the Debye length) of the electro-osmotic flow can be controlled by changing the concentration. For example, the flow region (the Debye length) becomes narrower by increasing the concentration, and the flow region (the Debye length) becomes wider by decreasing the concentration.

[4. Apparatus for Determining Nucleotide Sequences of Polynucleotides]

A apparatus for determining the nucleotide sequences of polynucleotides includes the control apparatus of the present invention. The control apparatus of the present invention has already been described, so configurations other than that will be described here.

The apparatus for determining the nucleotide sequences of polynucleotides of the present embodiment can be configured by combining any well-known sequencer and the control apparatus of the present invention. The components of the polynucleotides may be DNA or RNA. Further, the DNA and the RNA may be single-stranded or double-stranded.

For example, well-known sequencers include a type that decodes a base sequence by using a gel (e.g., plate gel, capillary gel) to separate a DNA fragment group to which fluorescent dyes have been added and detecting the type of fluorescent dye added to each DNA fragment.

In this case, the control apparatus of the present invention is disposed as part of the moving path of the DNA fragments formed by the gel, and a configuration for detecting fluorescence is disposed on the downstream side of the control apparatus. According to this configuration, when the DNA fragments to which the fluorescent dyes have been added pass through the surround electrode of the control apparatus of the present invention, the moving speed of the DNA fragments decelerates and thereafter the fluorescence is detected. As a result, the base sequence can be precisely determined.

Further, the apparatus for determining the nucleotide sequences of polynucleotides of the present invention can be configured by combining the "apparatus for determining nucleotide sequences of polynucleotides" disclosed in PCT/JP2011/054631 and the control apparatus of the present invention.

In this case also, like the case described above, a configuration for decoding the base sequence is disposed on the downstream side of the surround electrode of the control apparatus of the present invention on the moving path of the DNA fragments.

PCT/JP2011/054631 is incorporated for reference in the present specification.

WORKING EXAMPLE

1. Method of Evaluating Moving Speed of Substance

A method of evaluating the moving speed of a substance will be described.

Figure 5:
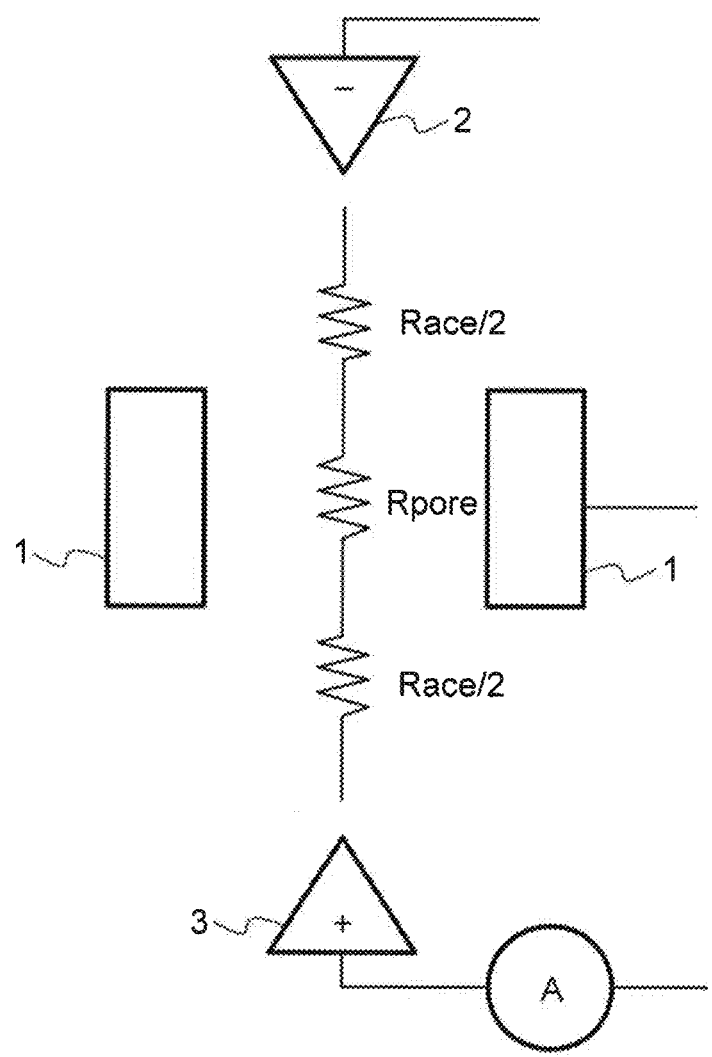
FIG. 5 is a drawing showing an example of an equivalent circuit of a control apparatus in a working example.

FIG. 5 shows an equivalent circuit of a control apparatus in the present working example, focusing on an ion current flowing through an internal space of a surround electrode 1 (an ion current flowing between a negative electrode 2 and a positive electrode 3).

As shown in FIG. 5, in the control apparatus of the present working example, when $R_{pore}$ denotes the resistance value of the internal space of the surround electrode 1 and $R_{ace}$ denotes the resistance value in the region outside the internal space, the total resistance value can be expressed as $R_{pore}+R_{ace}$. $R_{ace}$ is the sum of $R_{ace}/2$, which is the resistance value of the region on the negative electrode 2 side of the surround electrode 1, and $R_{ace}/2$, which is the resistance value of the region on the positive electrode 3 side of the surround electrode 1.

Figure 6A:
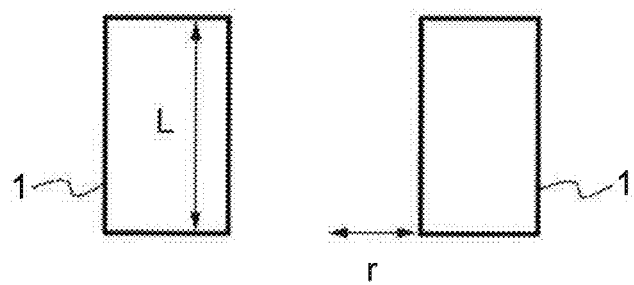
FIG. 6A is a drawing showing an example of the configuration of the control apparatus in the working example.

As shown in FIG. 6A, the resistance value (R) of the internal space of the surround electrode 1 can be represented by the following formula.

$$R = \rho L/\pi r^2 + \rho/2r \quad (1)$$

In the formula, ρ denotes the resistivity of the electrolytic solution, L denotes the length of the surround electrode 1 in the moving direction of the substance, and r denotes the radius of a circle in the cross section of a cylinder when the internal space of the surround electrode 1 is thought of as a substantially cylindrical shape.

Figure 6B:
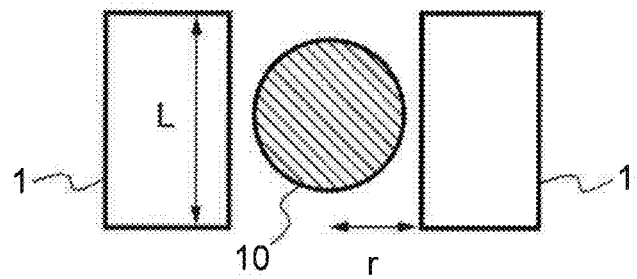
FIG. 6B is a drawing showing an example of the configuration of the control apparatus in the working example.

As shown in FIG. 6B, when the substance 10 exists in the internal space of the surround electrode 1, the value of "$\pi r^2$" in formula (1) changes. Specifically, if the substance 10 exists in the internal space of the surround electrode 1, the value of "$\pi r^2$" becomes smaller and, as a result, the value of "R" becomes larger. Additionally, if the value of "R" becomes larger, the current value of the ion current flowing through the internal space of the surround electrode 1 becomes smaller. Additionally, by observing the change in the current value of the ion current at each time, it becomes possible to grasp the moving situation of the substance 10 in the internal space of the surround electrode 1.

Figure 7A:
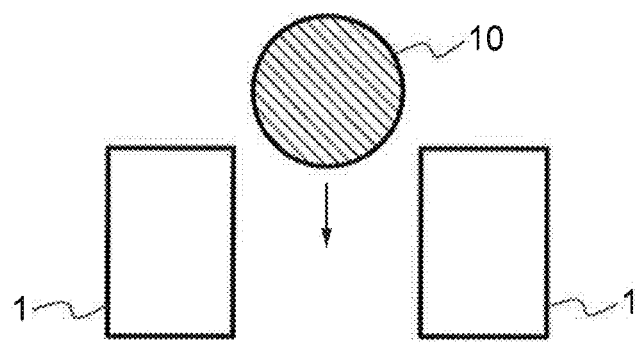
FIG. 7A is a drawing showing the state of the substance passing through the internal space of the surround electrode in the working example.
Figure 7B:
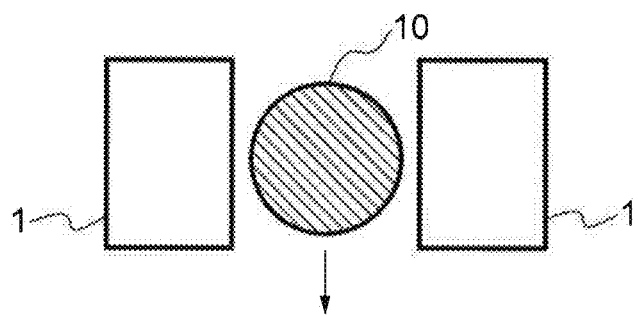
FIG. 7B is a drawing showing the state of the substance passing through the internal space of the surround electrode in the working example.
Figure 7C:
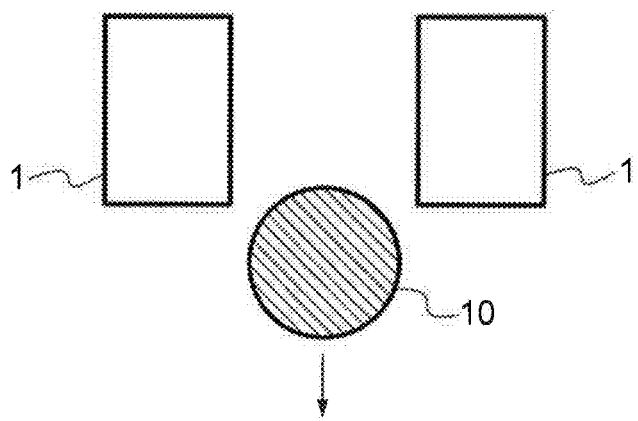
FIG. 7C is a drawing showing the state of the substance passing through the internal space of the surround electrode in the working example.

The change in the current value of the ion current at each time will be specifically described using FIG. 7A to FIG. 7C.

FIG. 7A to FIG. 7C show the state of the substance 10 passing through the internal space of the surround electrode 1. In FIG. 7A to FIG. 7C, the arrows indicate the moving direction of the substance 10.

FIG. 7A shows the substance 10 entering the internal space of the surround electrode 1, and part of the substance 10 is disposed in the internal space of the surround electrode 1. FIG. 7B shows the substance 10 after it has entered the internal space of the surround electrode 1, and the entire substance 10 is disposed in the internal space of the surround electrode 1. FIG. 7C shows the substance 10 emerging from the internal space of the surround electrode 1, and part of the substance 10 is disposed in the internal space of the surround electrode 1.

Figure 8:
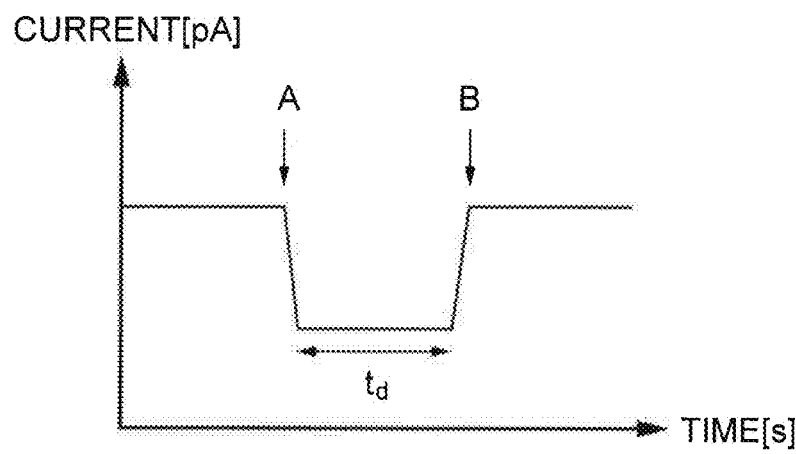
FIG. 8 is a graph showing a change in an ion current in the working example.

FIG. 8 shows an outline of the current value of the ion current flowing through the internal space of the surround electrode 1 in each of the states shown in FIG. 7A to FIG. 7C.

Before the substance 10 enters the internal space of the surround electrode 1, there is no change in the resistance value represented by formula (1), so a constant ion current flows.

"A" in FIG. 8 indicates the outline of the current value of the ion current flowing through the internal space of the surround electrode 1 in the state shown in FIG. 7A. At "A" in FIG. 8, the substance 10 starts to enter the internal space of the surround electrode 1, so the value of the resistance value represented by formula (1) starts to rise and, as a result, the current value of the ion current starts to fall.

"B" in FIG. 8 indicates the outline of the current value of the ion current flowing through the internal space of the surround electrode 1 in the state shown in FIG. 7C. At "B" in FIG. 8, the substance 10 starts to emerge from the internal space of the surround electrode 1, so the value of the resistance value represented by formula (1) starts to fall and, as a result, the current value of the ion current starts to rise.

The section between "A" and "B" in FIG. 8 indicates the outline of the current value of the ion current flowing through the internal space of the surround electrode 1 in the state shown in FIG. 7B. In the section between "A" and "B" in FIG. 8, the entire substance 10 is in the internal space of the surround electrode 1, so the current value of the ion current is maintained low.

"$t_d$" shown in FIG. 8 denotes the amount of time between "A" and "B". In other words, "$t_d$" is the amount of time in which the substance 10 exists in the internal space of the surround electrode 1. Additionally, "$t_d$" becomes shorter as the moving speed of the substance 10 increases, and becomes longer as the moving speed of the substance 10 decreases. Therefore, by measuring "$t_d$", increases and decreases in the moving speed of the substance 10 can be evaluated.

2. Manufacture of Control Apparatus

Figure 9:
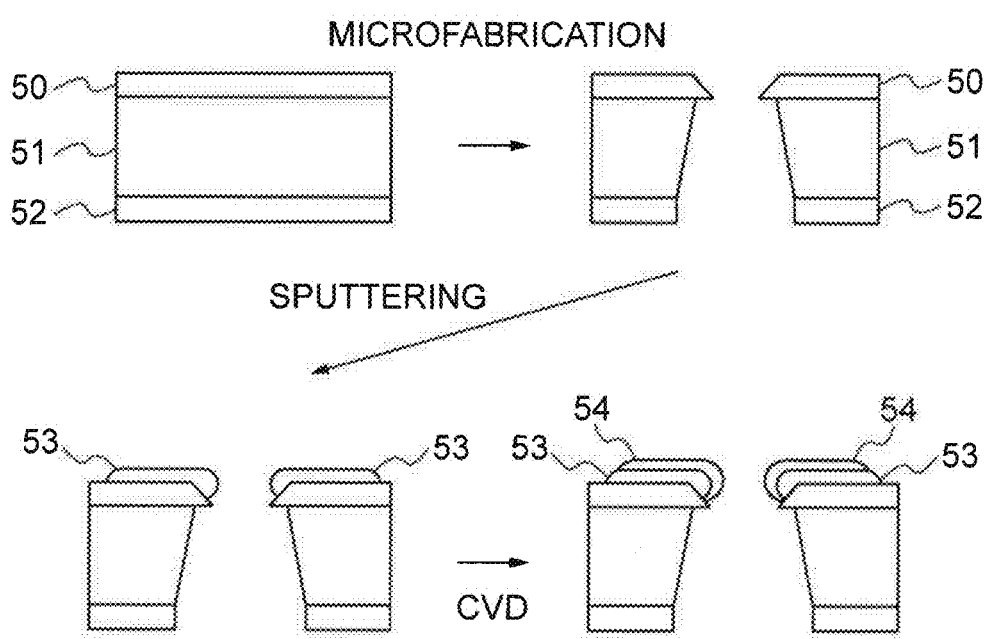
FIG. 9 is a drawing showing an example of a method of manufacturing the control apparatus in the working example.

The method of manufacturing the control apparatus of the present working example will be described using FIG. 9.

A through hole was formed by microfabrication (specifically, by performing electron beam lithography) in a silicon substrate 51, both of whose surfaces had been nitrided (the silicon substrate 51 has, as both of its surfaces, a silicon nitride membrane 50 and a silicon nitride membrane 52).

Next, a gate electrode 53 was formed by sputtering on the silicon nitride membrane 50. The specific configuration of the gate electrode 53 was "Pt (e.g., 2 nm)/Au (e.g., 70 nm)/Pt (e.g., 2 nm)/Ct (e.g., 2 nm)".

Next, a $SiO_2$ film 54 was formed by CVD, and the gate electrode 53 was covered by the $SiO_2$ film 54.

The gate electrode 53 covered by the $SiO_2$ film 54 formed in this way functioned as the surround electrode, and the substance passed through the gap (hole) formed in the gate electrode 53 covered by the $SiO_2$ film 54.

In the case of actually performing a test, PDMS having a flow channel formed therein was adhered to the top and bottom of the substrate manufactured as described above, and various types of samples were made to flow from one end of the flow channel toward the through hole.

Figure 10:
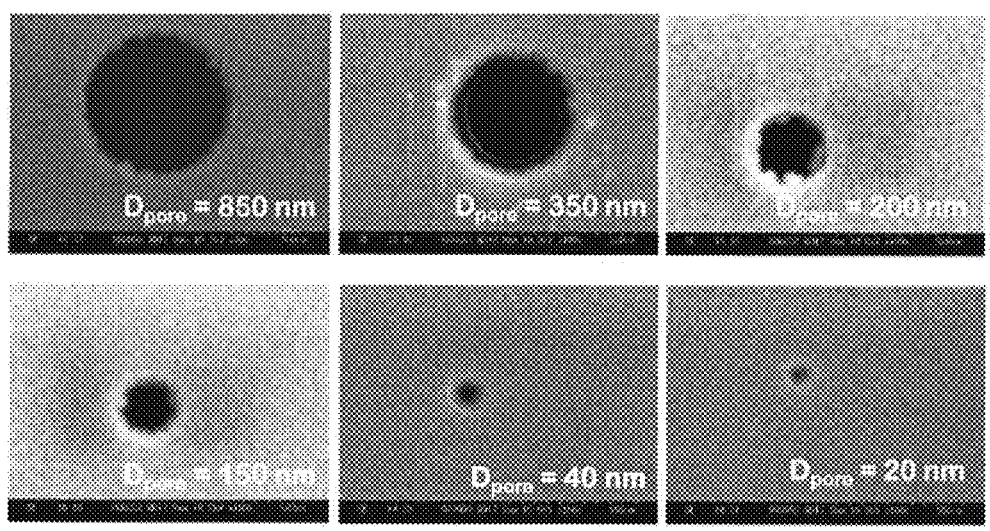
FIG. 10 is pictures showing through holes formed in surround electrodes in the working example.

FIG. 10 shows pictures of through holes that were formed in surround electrodes manufactured as described above.

As shown in FIG. 10, the diameters of the through holes were 850 nm, 350 nm, 200 nm, 150 nm, 40 nm, and 20 nm. This indicates that it is possible to manufacture through holes having desired diameters.

3. Inspection Relating to Control of Moving Speed of Substance (Polystyrene Particle)

In accordance with "<2. Manufacture of Control Apparatus>", a surround electrode was formed on the silicon nitride membrane 50 in which the diameter of the through hole was 1000 nm and whose thickness was 35 nm or 50 nm. Additionally, the surround electrode was used to manufacture the control apparatus shown in FIG. 3.

A polystyrene particle (having a diameter of 780 nm) was used as the substance 10 to be moved, TE buffer (having a pH of 8.0) was used as the medium disposed in the internal space of the surround electrode 1 covered by the $SiO_2$ film 54, and 0.2 V was used as the voltage applied between the negative electrode 2 and the positive electrode 3.

Additionally, the change in the moving speed of the polystyrene particle (specifically, the change in $t_d$) when the voltage applied to the surround electrode 1 was changed (Vg=0 V or Vg=−0.5 V) was observed.

Figure 11A:
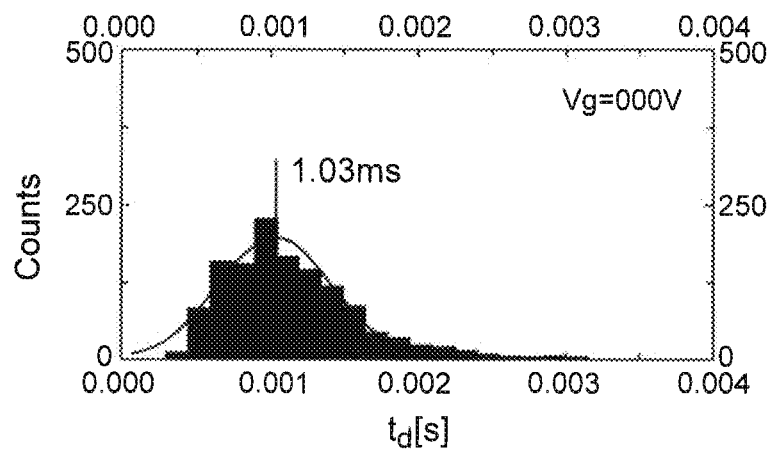
FIG. 11A is a graph showing a change in the moving speed of a substance (a polystyrene particle) in the working example.
Figure 11B:
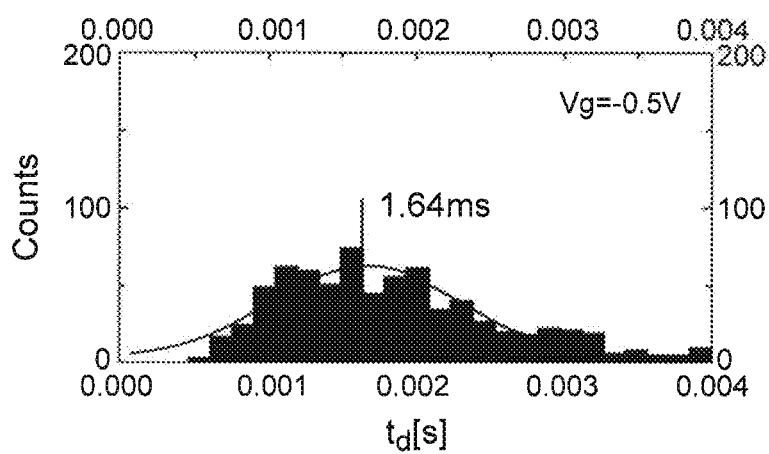
FIG. 11B is a graph showing a change in the moving speed of a substance (a polystyrene particle) in the working example.

FIG. 11A shows the result of the observation of the change in the moving speed of the polystyrene particle (specifically, the change in $t_d$) when the voltage applied to the surround electrode 1 was Vg=0 V in the case where the thickness of the silicon nitride membrane 50 was 35 nm. Further, FIG. 11B shows the result of the observation of the change in the moving speed of the polystyrene particle (specifically, the change in $t_d$) when the voltage applied to the surround electrode 1 was Vg=−0.5 V in the case where the thickness of the silicon nitride membrane 50 was 35 nm.

As shown in FIG. 11A, in the case of "Vg=0 V", "$t_d$" was 1.03 ms. On the other hand, as shown in FIG. 11B, in the case of "Vg=−0.5 V", "$t_d$" was 1.64 ms. This indicates that the moving speed of the polystyrene particle decelerated as a result of applying a voltage to the gate electrode 53.

Figure 12A:
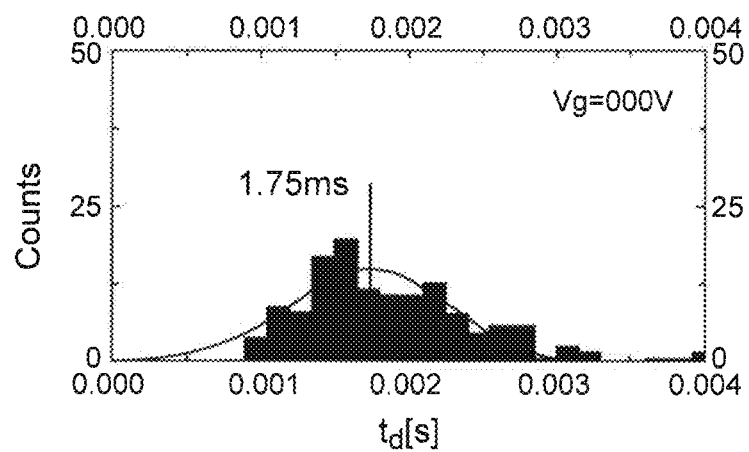
FIG. 12A is a graph showing a change in the moving speed of a substance (a polystyrene particle) in the working example.
Figure 12B:
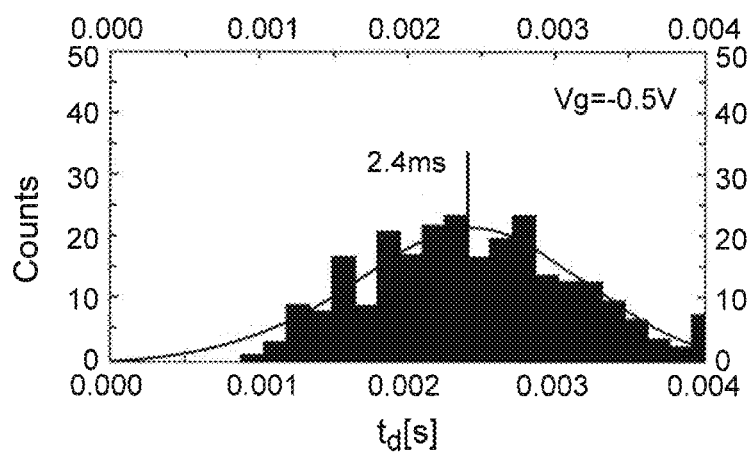
FIG. 12B is a graph showing a change in the moving speed of a substance (a polystyrene particle) in the working example.

FIG. 12A shows the result of the observation of the change in the moving speed of the polystyrene particle (specifically, the change in $t_d$) when the voltage applied to the surround electrode was Vg=0 V in the case where the thickness of the silicon nitride membrane 50 was 50 nm. Further, FIG. 12B shows the result of the observation of the change in the moving speed of the polystyrene particle (specifically, the change in $t_d$) when the voltage applied to the surround electrode was Vg=−0.5 V in the case where the thickness of the silicon nitride membrane 50 was 50 nm.

As shown in FIG. 12A, in the case of "Vg=0 V", "$t_d$" was 1.75 ms. On the other hand, as shown in FIG. 12B, in the case of "Vg=−0.5 V", "$t_d$" was 2.4 ms. This indicates that the moving speed of the polystyrene particle decelerated as a result of applying a voltage to the gate electrode 53 covered by the $SiO_2$ film 54.

4. Investigation Relating to Control of Moving Speed of Substance (DNA)

In accordance with "<2. Manufacture of Control Apparatus>", a surround electrode was formed on the silicon nitride membrane 50 in which the diameter of the through hole was 20 nm and whose thickness was 35 nm. Additionally, the surround electrode was used to manufacture the control apparatus shown in FIG. 3.

DNA (in a case where the shape of the DNA is regarded as a substantial cylinder, the length of the cylinder was substantially 150 nm and the diameter of the circle that was the cross section of the cylinder was substantially 2 nm) was used as the substance 10 to be moved, an aqueous solution containing KCl (concentration of KCl: 10 mM) was used as the medium disposed in the internal space of the surround electrode 1 covered by the $SiO_2$ film 54, and 0.2 V was used as the voltage applied between the negative electrode 2 and the positive electrode 3.

Additionally, the change in the moving speed of the DNA (specifically, the change in $t_d$) when the voltage applied to the surround electrode 1 was changed (Vg=0 V or Vg=−0.5 V) was observed.

Figure 13A:
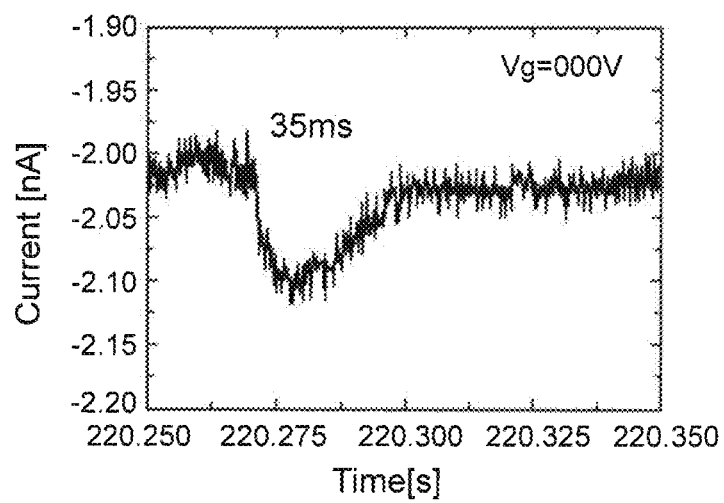
FIG. 13A is a graph showing a change in the moving speed of a substance (DNA) in the working example.
Figure 13B:
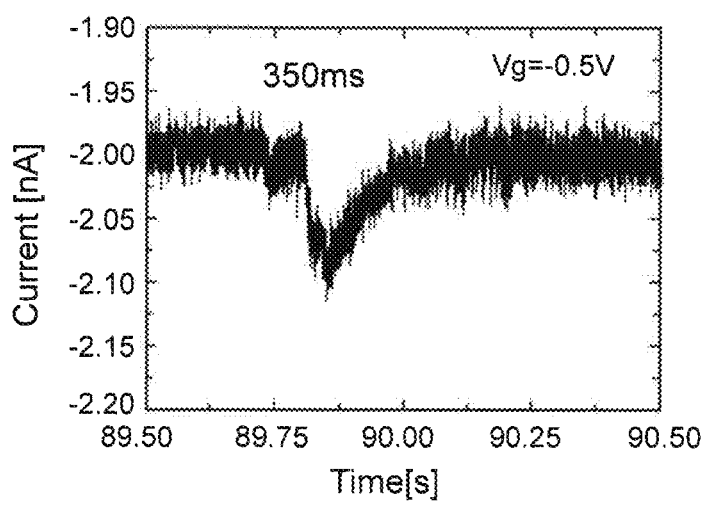
FIG. 13B is a graph showing a change in the moving speed of a substance (DNA) in the working example.

As shown in FIG. 13A, in the case of "Vg=0 V", "$t_d$" was 35 ms. On the other hand, as shown in FIG. 13B, in the case of "Vg=−0.5 V", "$t_d$" was 350 ms. This indicates that the moving speed of the DNA decelerated to about ¹⁄₁₀ as a result of applying the voltage to the gate electrode 53 covered by the $SiO_2$ film 54.

5. Effect of Voltage Applied to Surround Electrode on Moving Speed of Substance-1

The effect of the voltage applied to the surround electrode on the moving speed of the substance was investigated using the same technique as in <3> and <4>.

First, in accordance with "<2. Manufacture of Control Apparatus>", a surround electrode was formed on the silicon nitride membrane 50 in which the diameter of the through hole was 1000 nm and whose thickness was 35 nm. Moreover, the surround electrode was used to manufacture the control apparatus shown in FIG. 3.

A polystyrene particle (having a diameter of 780 nm) was used as the substance 10 to be moved, TE buffer (having a pH of 8.0) was used as the medium disposed in the internal space of the surround electrode 1 covered by the $SiO_2$ film 54, and 0.2 V was used as the voltage applied between the negative electrode 2 and the positive electrode 3.

Additionally, the change in the moving speed of the polystyrene particle (specifically, the change in $t_d$) when the voltage applied to the surround electrode 1 was changed (Vg=0 V, Vg=−0.25 V, Vg=−0.5 V, Vg=−1.0 V, or Vg=0.25 V) was observed.

As a result, in the case of "Vg=0 V", "$t_d$" was 1.03 ms, in the case of "Vg=−0.25 V", "$t_d$" was 0.99 ms, in the case of "Vg=−0.5 V", "$t_d$" was 1.64 ms, in the case of "Vg=−1.0 V", "$t_d$" was 35 ms, and in the case of "Vg=0.25 V", "$t_d$" was 0.90 ms.

That is, it became clear that, in the case of decelerating the substance, applying a voltage equal to or less than −0.5 V to the surround electrode covered by the $SiO_2$ film 54 is preferred. Further, in the case where the voltage of −1.0 V was applied to the surround electrode covered by the $SiO_2$ film 54, the moving speed of the substance was able to be decelerated to ⅟35 the moving speed in the case where a voltage was not applied (Vg=0 V).

On the other hand, it became clear that, in the case of accelerating the substance, applying a voltage equal to or greater than 0.25 V to the surround electrode covered by the $SiO_2$ film 54 is preferred.

When the diameter of the through hole was equal to or greater than 1.2 μm, the moving speed of the polystyrene particle did not change even when the voltage applied to the surround electrode was changed.

6. Effect of Voltage Applied to Surround Electrode on Moving Speed of Substance-2

The effect of the voltage applied to the surround electrode covered by the $SiO_2$ film 54 on the moving speed of the substance was investigated using the same technique as in <3> and <4>.

First, in accordance with "<2. Manufacture of Control Apparatus>", a surround electrode covered by the $SiO_2$ film 54 was formed on the silicon nitride membrane 50 in which the diameter of the through hole was 1000 nm and whose thickness was 50 nm. Moreover, the surround electrode was used to manufacture the control apparatus shown in FIG. 3. That is, the thickness of the silicon nitride membrane 50 was different between the control apparatus described in <6> and the control apparatus described in <5>.

A polystyrene particle (having a diameter of 780 nm) was used as the substance 10 to be moved, TE buffer (having a pH of 8.0) was used as the medium disposed in the internal space of the surround electrode 1, and 0.2 V was used as the voltage applied between the negative electrode 2 and the positive electrode 3.

Additionally, the change in the moving speed of the polystyrene particle (specifically, the change in $t_d$) when the voltage applied to the surround electrode 1 was changed (Vg=0 V, Vg=−0.5 V, or Vg=0.25 V) was observed.

As a result, in the case of "Vg=0 V", "$t_d$" was 1.75 ms, in the case of "Vg=−0.5 V", "$t_d$" was 2.4 ms, and in the case of "Vg=0.25 V", "$t_d$" was 1.4 ms.

That is, it became clear that, in the case of decelerating the substance, applying a voltage equal to or less than −0.5 V to the surround electrode is preferred. On the other hand, it became clear that, in the case of accelerating the substance, applying a voltage equal to or greater than 0.25 V to the surround electrode is preferred.

When the diameter of the through hole was equal to or greater than 1.2 μm, the moving speed of the polystyrene particle did not change even when the voltage applied to the surround electrode was changed.

7. Effect of Voltage Applied to Surround Electrode and Size of Through Hole on Moving Speed of Substance In accordance with "<2. Manufacture of Control Apparatus>", a surround electrode was formed on the silicon nitride membrane 50 in which the diameter of the through hole was 1200 nm and whose thickness was 50 nm. Moreover, the surround electrode was used to manufacture the control apparatus shown in FIG. 3.

A polystyrene particle (having a diameter of 780 nm) was used as the substance 10 to be moved, TE buffer (having a pH of 8.0) was used as the medium disposed in the internal space of the surround electrode 1, and 0.2 V was used as the voltage applied between the negative electrode 2 and the positive electrode 3.

Additionally, the change in the moving speed of the polystyrene particle (specifically, the change in $t_d$) when the voltage applied to the surround electrode 1 was changed (Vg=0 V, Vg=−0.5 V) was observed.

Figure 14A:
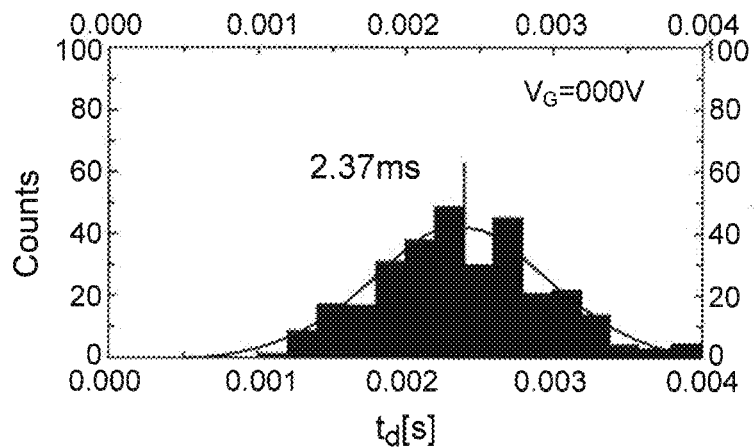
FIG. 14A is a graph showing that the moving speed of a substance (a polystyrene particle) do not change in the working example.
Figure 14B:
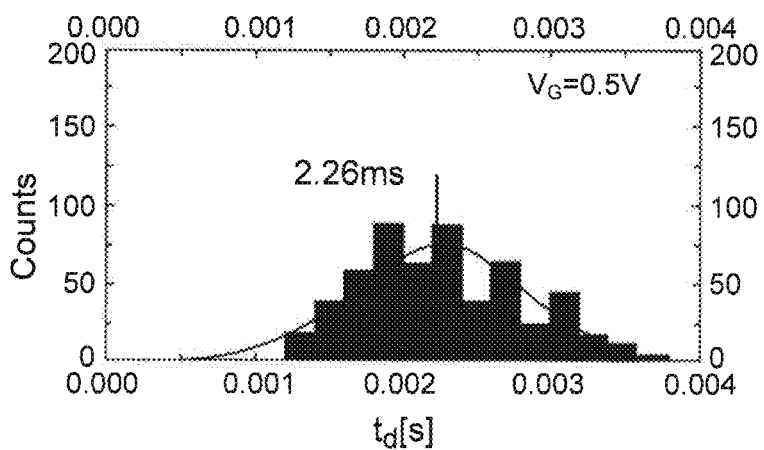
FIG. 14B is a graph showing that the moving speed of a substance (a polystyrene particle) do not change in the working example.

FIG. 14A and FIG. 14B show the results. As shown in FIG. 14A, in the case of "Vg=0 V", "$t_d$" was 2.37 ms, and as shown in FIG. 14B, in the case of "Vg=−0.5 V", "$t_d$" was 2.26 ms. That is, when the diameter of the through hole was equal to or greater than 1.2 μm, the effect of decelerating the moving speed of the polystyrene particle was low even when the voltage applied to the surround electrode was changed.

The present invention achieves the effect that it can control the moving speed of a substance to a desired speed. More specifically, the present invention achieves the effect that it can decelerate and can accelerate the moving speed of a substance. Further, the present invention achieves the effect that it can cause a substance to stop.

The present invention can be utilized in fields where it is necessary to control the moving speed of a substance.

For example, the present invention can be utilized in next-next generation sequencers promoted by the National Institutes of Health (NIH) of the U.S.A. and can be applied to next-next generation sequencers that do not require the amplification of DNA by PCR and the chemical modification of DNA. Further, the present invention can be applied to high-sensitivity sensors that detect, by single molecule, biomolecules such as influenza viruses and allergens.

The invention claimed is:

1. A method for regulating a flow rate of a biomolecule through a fluid flow path, comprising:
   (a) subjecting a solution comprising said biomolecule to flow through said fluid flow path having a length using an electric field provided by a pair of electrodes at opposing ends of said fluid flow path, wherein said fluid flow path includes an internal space comprising different electrode sections that substantially oppose one another along said length, wherein each of said different electrode sections includes a non-conductive film adjacent to a conductive material, which non-conductive film is in contact with said solution;
   (b) changing said flow rate of said biomolecule through said fluid flow path by applying a positive or negative voltage to said different electrode sections; and
   (c) detecting said biomolecule or a portion thereof upon changing said flow rate of said biomolecule through said fluid flow path.

2. The method of claim 1, wherein said solution includes an electrolyte.

3. The method of claim 1, wherein said biomolecule is charged.

4. The method of claim 1, wherein (b) comprises supplying a gate voltage from about −3 V to 3 V to said different electrode sections.

5. The method of claim 1, wherein said fluid flow path has a first width (Y) and said biomolecule in said fluid flow path has a second width (X), and wherein $0.5 < X/Y < 1$.

6. The method of claim 5, wherein $0.7 < X/Y < 1$.

7. The method of claim 6, wherein $0.8 < X/Y < 1$.

8. The method of claim 1, wherein applying said positive or negative voltage to said different electrode sections generates electro-osmotic flow in said internal space.

9. The method of claim 1, wherein each of said different electrode sections is formed of a metallic material.

10. The method of claim 1, wherein said non-conductive film is a semiconductor oxide film.

11. The method of claim 1, wherein said fluid flow path includes a layer of charge adjacent to said different electrode sections having a Debye length.

12. The method of claim 1, wherein said biomolecule is a nucleic acid molecule.

13. The method of claim 1, wherein said biomolecule is a protein.

14. The method of claim 1, wherein said pair of electrodes includes a first electrode and a second electrode, and wherein (b) comprises applying said positive or negative voltage to said first electrode.

15. The method of claim 1, wherein said conductive material is covered by said non-conductive film.

16. A system for regulating a flow rate of a biomolecule through a fluid flow path, comprising:
  (a) a pair of electrodes that provide an electric field to subject a solution comprising said biomolecule to flow;
  (b) a fluid flow path having a length and with a cross-section that is sufficient to permit said solution having said biomolecule to flow therethrough, wherein said pair of electrodes is at opposing ends of said fluid flow path, and wherein said fluid flow path includes an internal space comprising different electrode sections that substantially oppose one another along said length, wherein each of said different electrode sections includes a non-conductive film adjacent to a conductive material, which non-conductive film is in contact with said solution;
  (c) a voltage application member that applies a positive or negative voltage to said different electrode sections to change said flow rate of said biomolecule through said fluid flow path; and
  (d) a detector that detects said biomolecule or a portion thereof upon changing said flow rate of said biomolecule through said fluid flow path.

17. The system of claim 16, wherein said solution includes an electrolyte.

18. The system of claim 16, wherein said biomolecule is charged.

19. The system of claim 16, wherein voltage application member supplies a gate voltage from about −3 V to 3 V to said different electrode sections.

20. The system of claim 16, wherein said fluid flow path has a first width (Y) and said biomolecule in said fluid flow path has a second width (X), and wherein $0.5 < X/Y < 1$.

21. The system of claim 20, wherein $0.7 < X/Y < 1$.

22. The system of claim 21, wherein $0.8 < X/Y < 1$.

23. The system of claim 16, wherein said non-conductive film is a semiconductor oxide film.

24. The system of claim 16, wherein said fluid flow path includes a layer of charge adjacent to said different electrode sections having a Debye length.

25. The system of claim 16, wherein said application of said positive or negative voltage to said different electrode sections generates electro-osmotic flow in said internal space.

26. The system of claim 16, wherein said biomolecule is a nucleic acid molecule.

27. The system of claim 16, wherein said biomolecule is a protein.

28. The system of claim 16, wherein said pair of electrodes includes a first electrode and a second electrode, and wherein said voltage application member applies said positive or negative voltage to said first electrode.

29. The system of claim 16, wherein said conductive material is covered by said non-conductive film.

* * * * *